US010123914B2

(12) United States Patent
Kobayashi et al.

(10) Patent No.: US 10,123,914 B2
(45) Date of Patent: Nov. 13, 2018

(54) UNDERWEAR-STYLE ABSORBENT ARTICLE

(71) Applicant: KAO CORPORATION, Tokyo (JP)

(72) Inventors: Kenji Kobayashi, Utsunomiya (JP); Naoki Tamura, Utsunomiya (JP)

(73) Assignee: KAO CORPORATION, Tokyo (JP)

(*) Notice: Subject to any disclaimer, the term of this patent is extended or adjusted under 35 U.S.C. 154(b) by 486 days.

(21) Appl. No.: 14/890,809

(22) PCT Filed: Apr. 24, 2014

(86) PCT No.: PCT/JP2014/061503
§ 371 (c)(1),
(2) Date: Nov. 12, 2015

(87) PCT Pub. No.: WO2014/185242
PCT Pub. Date: Nov. 20, 2014

(65) Prior Publication Data
US 2016/0106601 A1    Apr. 21, 2016

(30) Foreign Application Priority Data

May 13, 2013 (JP) ................................. 2013-101237

(51) Int. Cl.
*A61F 13/15*    (2006.01)
*A61F 13/20*    (2006.01)
(Continued)

(52) U.S. Cl.
CPC .. *A61F 13/49058* (2013.01); *A61F 13/15593* (2013.01); *A61F 13/496* (2013.01);
(Continued)

(58) Field of Classification Search
CPC .......... A61F 13/15593; A61F 13/49012; A61F 13/49019; A61F 13/49058; A61F 13/496;
(Continued)

(56) References Cited

U.S. PATENT DOCUMENTS 7,758,558 B2    7/2010  Otsubo
9,011,404 B2 *  4/2015  Kobayashi ........ A61F 13/15804
                                                        156/163
(Continued)

FOREIGN PATENT DOCUMENTS

CN    1315448 C    5/2007
CN    202283309 U  6/2012
(Continued)

OTHER PUBLICATIONS

International Preliminary Report on Patentability and English translation of the Written Opinion of the International Searching Authority issued in the corresponding International Application No. PCT/JP2014/061503 dated Nov. 26, 2015.
(Continued)

Primary Examiner — Michele M Kidwell
(74) Attorney, Agent, or Firm — Birch, Stewart, Kolasch & Birch, LLP

(57) ABSTRACT

In this diaper (1A), both lateral side edge portions (2a, 2b) of an outer cover (2) to which an absorbent assembly (3) is fixed are bonded together, so as to form a pair of side seals (4). In a fixing part (7) where the outer cover (2) and the absorbent assembly (3) are fixed, the outer cover (2) has a weak-functioning region (WT) in which the elastic function is reduced. In each outer lateral side of the weak-functioning region (WT) and in each side seal (4), a lateral-side adhesion region (IT) and a side-seal adhesion region (OT) are formed, respectively, in each of which elastic members (24) are fixed between an outer sheet (22) and an inner sheet (23) by an adhesive (8). In each lateral-side adhesion region (IT) and each side-seal adhesion region (OT), the basis weight of the adhesive (8) in a section (IP, OP) where the elastic member (24) is arranged is higher than the basis weight of the adhesive (8) in a section (IN, ON) between a pair of adjacent elastic members (24), and sections with high and low basis (Continued)

weights in adhesive (8) alternate repeatedly in the Y direction.

20 Claims, 12 Drawing Sheets

(51) Int. Cl.
    *A61F 13/49*     (2006.01)
    *A61F 13/496*     (2006.01)
    *A61F 13/539*     (2006.01)

(52) U.S. Cl.
    CPC .. *A61F 13/49012* (2013.01); *A61F 13/49019* (2013.01); *A61F 13/4963* (2013.01); *A61F 13/539* (2013.01); *A61F 2013/5395* (2013.01)

(58) Field of Classification Search
    CPC ................ A61F 13/4963; A61F 13/539; A61F 2013/5395
    See application file for complete search history.

(56) References Cited

U.S. PATENT DOCUMENTS

| | | |
|---|---|---|
| 2005/0131374 A1 | 6/2005 | Otsubo et al. |
| 2008/0114321 A1 | 5/2008 | Otsubo |
| 2010/0076394 A1* | 3/2010 | Hayase ............. A61F 13/15593 604/385.29 |
| 2012/0095429 A1 | 4/2012 | Kobayashi et al. |
| 2012/0095431 A1 | 4/2012 | Tsai et al. |
| 2012/0310193 A1* | 12/2012 | Ostertag ........... A61F 13/15593 604/365 |
| 2013/0046266 A1* | 2/2013 | Kawakami ............ A61F 13/496 604/385.3 |
| 2013/0060219 A1* | 3/2013 | Mukai ............... A61F 13/49058 604/385.3 |

FOREIGN PATENT DOCUMENTS

| | | |
|---|---|---|
| EA | 014863 B1 | 2/2011 |
| EP | 1547558 A1 | 6/2005 |
| JP | 7-213553 A | 8/1995 |
| JP | 10-000081 U | 3/1998 |
| JP | 2004-298362 A | 10/2004 |
| JP | 2004-337388 A | 12/2004 |
| JP | 2005-211673 A | 8/2005 |
| JP | 2007-151597 A | 6/2007 |
| JP | 2008-142341 A | 6/2008 |
| JP | 2008-295930 A | 12/2008 |
| JP | 2009-148447 A | 7/2009 |
| JP | 2009-297096 A | 12/2009 |
| JP | 2011-10839 A | 1/2011 |
| JP | 2011-025006 A | 2/2011 |
| JP | 2011-115304 A | 6/2011 |
| JP | 2011-234847 A | 11/2011 |
| JP | 2013-034850 A | 2/2013 |
| JP | 2013-132331 A | 7/2013 |
| JP | 2013-146549 A | 8/2013 |
| JP | 2014-004115 A | 1/2014 |
| TW | M405257 U1 | 6/2011 |
| TW | M422407 U1 | 2/2012 |
| WO | WO 2007/037390 A1 | 4/2007 |
| WO | WO 2013/005423 A1 | 1/2013 |

OTHER PUBLICATIONS

Extended European Search Report dated Dec. 15, 2016, for European Application No. 14798104.7.

International Search Report issued in PCT/JP2014/061503, dated Jun. 17, 2014.

* cited by examiner

UNDERWEAR-STYLE ABSORBENT ARTICLE

TECHNICAL FIELD

The present invention relates to a pull-on absorbent article such as a disposable diaper.

BACKGROUND ART

There have conventionally been known pull-on absorbent articles made by fixing an absorbent assembly, which includes an absorbent member, to an outer cover formed by fixing a plurality of thread-form elastic members in a stretched state between an outer sheet and an inner sheet.

For example, Patent Literature 1 discloses a pull-on absorbent article including an outer cover in which a plurality of auxiliary elastic members are secured in a stretched state and extend along a waist-surrounding direction so as to cross a core.

Patent Literature 2 discloses a pull-on absorbent article including an outer cover sheet in which a plurality of below-waist elastic extensible members, which form shirring around the below-waist section, are fixed between an upper nonwoven fabric and a lower nonwoven fabric, and in which the below-waist elastic extensible members are cut in a region overlapping an absorbent assembly.

CITATION LIST

Patent Literature

Patent Literature 1: U.S. Pat. No. 7,758,558 (B2)
Patent Literature 2: WO 2007037390 (A1)

SUMMARY OF INVENTION

In the pull-on absorbent article disclosed in Patent Literature 1, the auxiliary elastic members on the absorbent member, which constitutes the core, are secured in a continuous manner, and thus cause the absorbent member to contract. The contraction of the absorbent member may, for example, impair the outer appearance of the pull-on absorbent article or give rise to leakage due to the creases formed in the absorbent member.

The pull-on absorbent article disclosed in Patent Literature 2 includes an outer cover sheet in which the below-waist elastic extensible members are cut in a region overlapping the absorbent assembly, and thus, the absorbent assembly is less likely to contract.

In the pull-on absorbent article disclosed in Patent Literature 2, however, in order to form shining around the below-waist section, the below-waist elastic extensible members are fixed between the upper nonwoven fabric and the lower nonwoven fabric by applying an adhesive to sections corresponding to the below-waist elastic extensible members in the shining-forming section. Forming shining around the below-waist section by applying the adhesive in this fashion, however, hardens the shining section around the below-waist section, and also impairs texture. In contrast, if the below-waist elastic extensible members are fixed between the upper nonwoven fabric and the lower nonwoven fabric simply by applying an adhesive in a planar form only to sections corresponding to the below-waist elastic extensible members at both ends in the width direction outside the shirring-forming section, the sections where the adhesive is applied will become stiff, and also, the below-waist elastic extensible members may fall out due to contractile force.

Accordingly, the present invention relates to a pull-on absorbent article in which the elastic members are less likely to form creases in the absorbent member, thereby improving outer appearance, and also in which texture is improved and the elastic members are less likely to fall out.

The present invention relates to A pull-on absorbent article including: an outer cover including an outer sheet that constitutes an outer surface, an inner sheet that is arranged on an inner surface side of the outer sheet, and a plurality of thread-form elastic members that are arranged in a stretched state between the outer sheet and the inner sheet; and an absorbent assembly that is fixed to the inner sheet of the outer cover; and both lateral side edge portions of the outer cover's front portion which is arranged on a front side of a wearer are bonded with respective lateral side edge portions of the outer cover's rear portion which is arranged on a rear side of the wearer so as to form a pair of side seals, a waist opening, and a pair of leg openings. In a fixing part where the outer cover and the absorbent assembly are fixed, the outer cover has a weak-functioning region in which the plurality of elastic members are each divided into a plurality of pieces and the elastic members' elastic function is reduced. In respective outer lateral sides of the weak-functioning region, lateral-side adhesion regions are formed in which the elastic members are fixed between the outer sheet and the inner sheet by an adhesive. In the vicinity of the respective side seals, side-seal adhesion regions are formed in which the elastic members are fixed between the outer sheet and the inner sheet by an adhesive. Between the lateral-side adhesion region and the side-seal adhesion region, the elastic members are not fixed between the outer sheet and the inner sheet. In each of the lateral-side adhesion regions and each of the side-seal adhesion regions, the basis weight of the adhesive in a section where the elastic member is arranged is higher than the basis weight of the adhesive in a section between adjacent elastic members, and sections having a high basis weight and sections having a low adhesive basis weight alternate repeatedly in a longitudinal direction of the pull-on absorbent article.

DESCRIPTION OF EMBODIMENTS

A pull-on absorbent article of the invention is described below according to a preferred first embodiment thereof with reference to the drawings.

Figure 1:
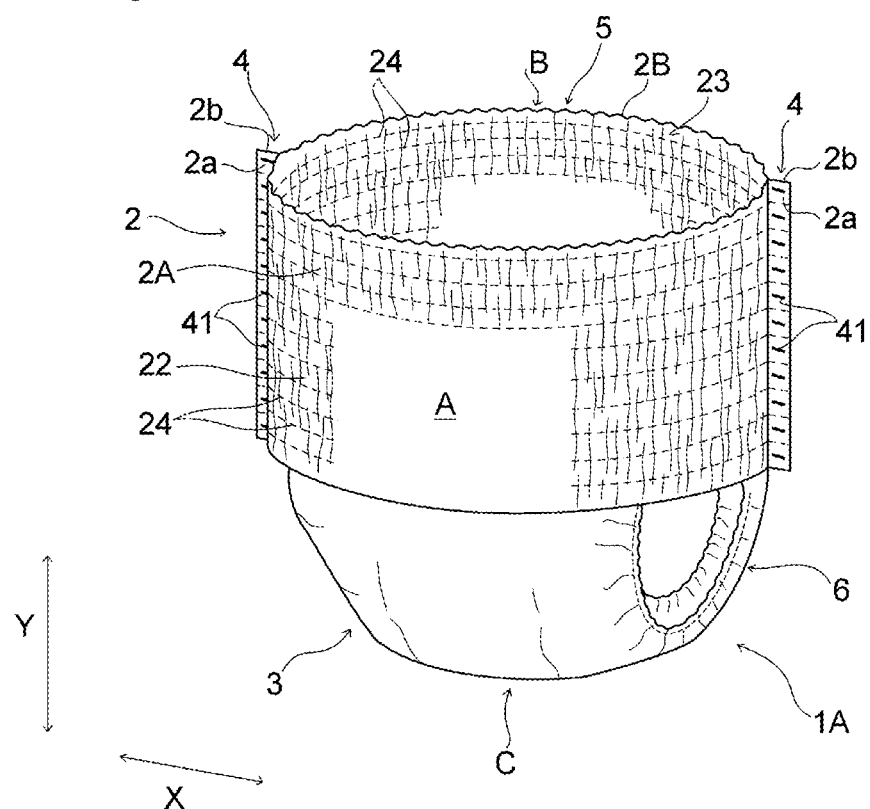
FIG. 1 is a perspective view of a pull-on disposable diaper according to a first embodiment of the invention.
Figure 2:
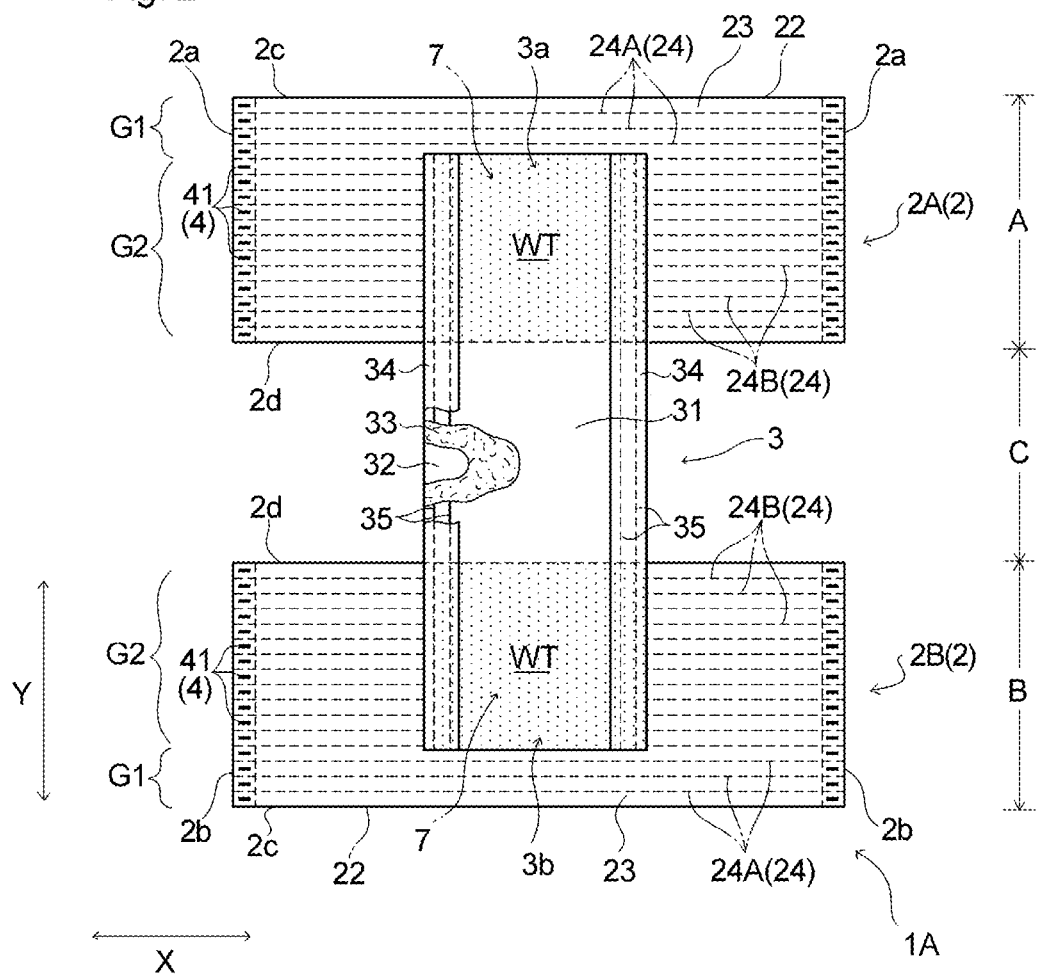
FIG. 2 is a partially cutaway plan view illustrating a state in which the pull-on disposable diaper illustrated in FIG. 1 is spread out and stretched. A "spread-out and stretched state" refers to a state in which the side seals are torn open to bring the pull-on absorbent article in a spread-out (developed) state, and the elastic members in various parts of the spread-out absorbent article are stretched so that the absorbent article is spread to its designed size (size when the absorbent article is spread out in a planar manner in a state where the effect of the elastic members is completely eliminated).

As illustrated in FIGS. 1 and 2, a pull-on disposable diaper 1A (referred to hereinafter also as "diaper 1A") according to a first embodiment of the invention includes: an outer cover 2 including an outer sheet 22 that constitutes an outer surface, an inner sheet 23 that is arranged on the inner surface side of the outer sheet 22, and a plurality of thread-form elastic members 24 that are arranged in a stretched state between the outer sheet 22 and the inner sheet 23; and an absorbent assembly 3 that is fixed to the inner sheet 23 of the outer cover 2 in a fixing part. Both lateral side edge portions 2a of the outer cover 2's front portion A which is arranged on a front side of a wearer are bonded with respective lateral side edge portions 2b of the outer cover 2's rear portion B which is arranged on a rear side of the wearer so as to form a pair of side seals 4, a waist opening 5, and a pair of leg openings 6, 6.

More specifically, as illustrated in FIGS. 1 and 2, the diaper 1A includes: a front portion A arranged on the wearer's front side when worn; a rear portion B arranged on the wearer's rear side when worn; and a crotch portion C located between the front portion A and the rear portion B and arranged in the wearer's crotch section when worn. The longitudinal direction of the diaper (absorbent article) 1A is the direction extending from the front portion A to the rear portion B via the crotch portion C, or the direction opposite therefrom (i.e., the Y direction in the figure). The lateral direction of the diaper (absorbent article) 1A is the direction along the direction around the wearer's waist/hip, and is a direction intersecting with the longitudinal direction of the diaper (absorbent article) 1A (i.e., the X direction in the figure).

As illustrated in FIGS. 1 and 2, the outer cover 2 of the diaper 1A includes: a rectangular front panel 2A that is arranged on the wearer's front side when worn and that is long in the X direction; and a rectangular rear panel 2B that is arranged on the wearer's rear side when worn and that is long in the X direction. In the diaper 1A, the absorbent assembly 3 is arranged and fixed so as to extend between the central portion, in the X direction, of the front panel 2A and the central portion, in the X direction, of the rear panel 2B. The diaper 1A is formed by bonding the lateral side edge portions 2a, 2a of the front panel 2A with the respective lateral side edge portions 2b, 2b of the rear panel 2B at the pair of side seals 4, 4.

This is described in further detail below.

As illustrated in FIG. 2, in the diaper 1A of the first embodiment, the absorbent assembly 3 includes: a liquid-permeable topsheet 31; a liquid-impermeable or water-repellent backsheet 32; and a liquid-retentive absorbent member 33 interposed between the topsheet 31 and the backsheet 32. The absorbent assembly 3 is formed in a rectangular form that is long in the Y direction. The absorbent member 33 includes: an absorbent core constituted by a fiber aggregate (which may be a nonwoven fabric) made of e.g. pulp fiber, or an absorbent core in which water-absorbing polymer particles are retained in the aforementioned absorbent core; and a core-wrap sheet (not illustrated) that covers the absorbent core. The absorbent member 33 is also formed in a rectangular form that is long in the Y direction.

As illustrated in FIG. 2, side cuffs 34, 34, each made of a liquid-resistant/water-repellent and air-permeable material, are formed on the absorbent assembly 3's respective lateral sides that extend along the Y direction. Each side cuff 34 includes side-cuff elastic members 35 arranged in the vicinity of the side cuff 34's free end and in a stretched state. When the diaper 1A is worn, the contraction of the side-cuff elastic members 35 causes the side cuffs 34 to stand up, thereby preventing fluid from flowing outward from the absorbent assembly 3 in the X direction. As for the topsheet 31, the backsheet 32, and the absorbent core and the core-wrap sheet of the absorbent member 33, it is possible to use materials similar to those conventionally used in this type of absorbent article. On the outer side of the absorbent assembly 3, an outer cover sheet made of e.g. a nonwoven fabric or a film may be arranged so as to overlap the backsheet 32.

As illustrated in FIG. 2, the absorbent assembly 3's one end portion 3a in the Y direction is fixed by an adhesive in a fixing part 7 to the central portion, in the X direction, of the front panel 2A, and the other end portion 3b in the Y direction is fixed by an adhesive in a fixing part 7 to the central portion, in the X direction, of the rear panel 2B. It should be noted that, although the absorbent assembly 3 and the front panel 2A/rear panel 2B are fixed together by an adhesive in the first embodiment, the fixing part may be formed by other known fixing methods, such as heat sealing, high-frequency sealing, and ultrasonic sealing.

As illustrated in FIG. 2, in the diaper 1A of the first embodiment, the front panel 2A has a rectangular shape that is long in the X direction in a state where the diaper 1A is spread out and stretched, and includes a pair of right and left lateral side edge portions 2a, 2a that extend along the Y direction, and a pair of upper and lower end edge portions 2c, 2d (upper end edge portion 2c, lower end edge portion 2d) that extend along the X direction. Likewise, the rear panel 2B has a rectangular shape that is long in the X direction, and includes a pair of right and left lateral side edge portions 2b, 2b that extend along the Y direction, and a pair of upper and lower end edge portions 2c, 2d (upper end edge portion 2c, lower end edge portion 2d) that extend along the X direction.

Figure 3:
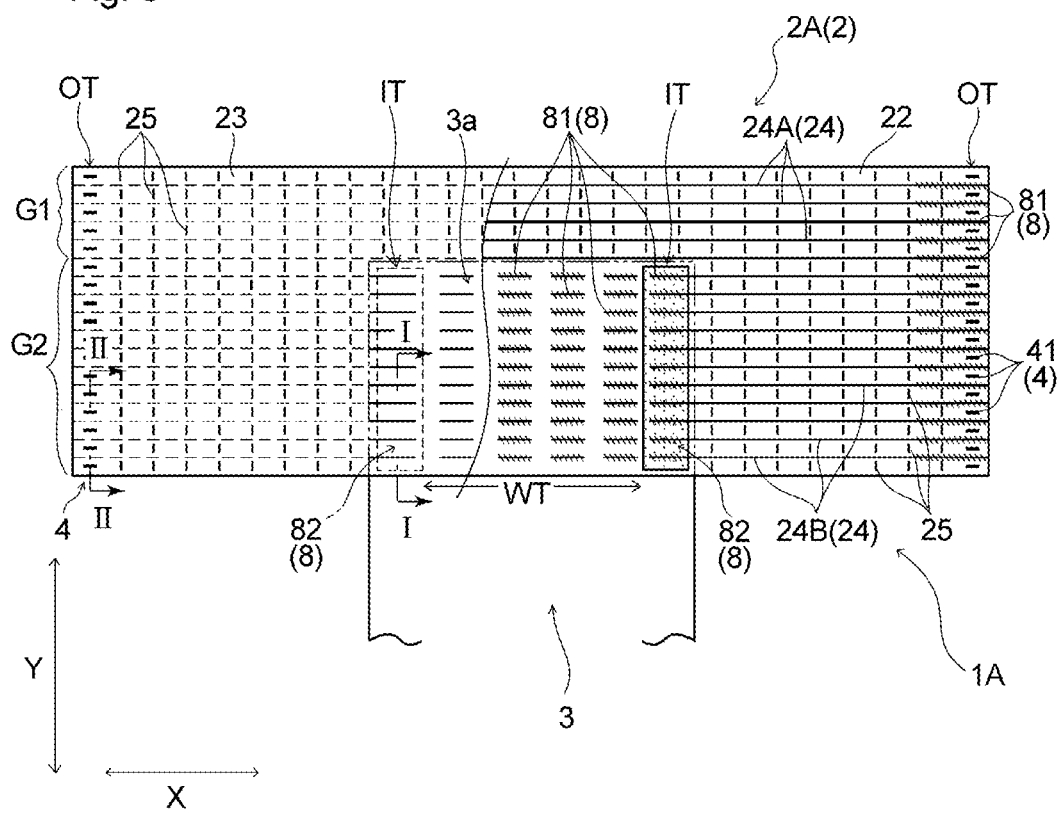
FIG. 3 is a partially cutaway enlarged view of a front portion side, in a stretched state, of the pull-on disposable diaper illustrated in FIG. 1 as viewed from the diaper's inner surface side.

As illustrated in FIGS. 2 and 3, each of the front panel 2A and the rear panel 2B in the diaper 1A includes: an outer sheet 22 that constitutes the diaper's outer surface; an inner sheet 23 that is arranged on the inner surface side of the outer sheet 22; and a plurality of thread-form elastic members 24 that are arranged between the outer sheet 22 and the inner sheet 23 in a state stretched in the X direction and that are arranged with intervals therebetween in the Y direction. Each panel is formed by fixing the plurality of thread-form elastic members 24 between the outer sheet 22 and the inner sheet 23 by an adhesive 8. A waist elasticized portion G1 and a below-waist elasticized portion G2 that are elastic in the X direction are formed in each of the front panel 2A and the rear panel 2B. The adhesive 8 for fixing the elastic members 24 will be described in detail further below.

For the outer sheet 22 and the inner sheet 23, it is possible to use various sheet materials conventionally used in this type of article without particular limitation, but it is preferable to use a nonwoven fabric, and particularly from the viewpoint of softness etc., it is preferable to use a single-layer nonwoven fabric constituted by e.g. air-through nonwoven fabric, heat-rolled nonwoven fabric, spun-laced nonwoven fabric, spun-bonded nonwoven fabric, or melt-blown nonwoven fabric, or a laminated nonwoven fabric including two or more layers. Instead, the outer sheet and the inner sheet may each be a sheet made by integrating the aforementioned nonwoven fabric and a film. As for materials forming the elastic members 24, it is possible to use various known elastic materials used in absorbent articles, such as disposable diapers and sanitary napkins, without particular limitation. Examples of elastic materials include synthetic rubber, such as styrene-butadiene, butadiene, isoprene, or neoprene, natural rubber, EVA, elastic polyolefins, polyurethane, etc. As for the shape of the elastic members, it is possible to preferably employ: thread-type members (rubber threads, etc.) having e.g. a rectangular, square, circular, or polygonal cross-sectional shape; tape-shaped members (flat rubber bands, etc.); or multi-filament-type threads.

Preferable materials for the adhesive 8 for fixing the elastic members 24 as well as adhesives for bonding the various members include, for example, thermoplastic polymers, such as amorphous polyolefins, ethylene-vinyl acetate copolymer (EVA), ethylene-acrylic acid ester copolymer (EEA), styrene-butadiene-styrene block copolymer (SBS), styrene-isoprene-styrene block copolymer (SIS), styrene-ethylene/butylene-styrene block copolymer (SEBS), and styrene-ethylene/propylene-styrene block copolymer (SEPS), and mixtures of the above. The adhesives are preferably hot-melt adhesives.

As illustrated in FIGS. 2 and 3, in each of the front panel 2A and the rear panel 2B, the waist elasticized portion G1 is formed more outward in the Y direction than the absorbent assembly 3's end portion 3a, 3b in the Y direction. In each of the front panel 2A and the rear panel 2B, the below-waist elasticized portion G2 is formed more inward in the Y direction than the waist elasticized portion G1. In the front panel 2A, a plurality of elastic members 24A are arranged in the waist elasticized portion G1, and a plurality of elastic members 24B are arranged in the below-waist elasticized portion G2. As in the front panel 2A, also in the rear panel 2B, a plurality of elastic members 24A are arranged in the waist elasticized portion G1, and a plurality of elastic members 24B are arranged in the below-waist elasticized portion G2.

As illustrated in FIG. 3, in the waist elasticized portion G1 and the below-waist elasticized portion G2 in the diaper 1A of the first embodiment, the outer sheet 22 and the inner sheet 23 are bonded by a multitude of bonded portions 25 formed in a scattered manner.

More specifically, in each of the elasticized portions G1 and G2 in each of the front panel 2A and the rear panel 2B, a plurality of bonded-portion rows—each including a plurality of bonded portions 25 arranged intermittently in the X direction—are formed in the Y direction. That is, in the waist elasticized portion G1, each elastic member 24A is arranged between: a bonded-portion row that includes a plurality of bonded portions 25 arranged intermittently in the X direction; and another bonded-portion row that is adjacent, in the Y direction, to the aforementioned bonded-portion row and that includes a plurality of bonded portions 25 arranged intermittently in the X direction. In the below-waist elasticized portion G2, each elastic member 24B is arranged between: a bonded-portion row that includes a plurality of bonded portions 25 arranged intermittently in the X direction; and another bonded-portion row that is adjacent, in the Y direction, to the aforementioned bonded-portion row and that includes a plurality of bonded portions 25 arranged intermittently in the X direction.

In this way, in each of the elasticized portions G1 and G2 in each of the front panel 2A and the rear panel 2B, each elastic member 24 (24A, 24B) is arranged so as to be passed between bonded portions 25, 25 that are adjacent to one another in the Y direction.

In the diaper 1A, the elastic members 24A, 24B arranged in the front panel 2A are arranged at substantially the same extension rate as the elastic members 24A, 24B arranged in the rear panel 2B.

More specifically, it is preferable that the size of a single thread of each elastic member 24A arranged in the waist elasticized portion G1 and each elastic member 24B arranged in the below-waist elasticized portion G2 is about 11 dtex to 1870 dtex. It is preferable to arrange such thread-form elastic members 24A, 24B such that the extension rate is 200% or higher. It should be noted that the extension rate is the percentage of the elastic member's length in a stretched state with respect to its natural length; for example, if a 10-cm-long elastic member is stretched to 20 cm, the extension rate is 200%.

It is preferable that the arrangement interval between adjacent thread-form elastic members 24 (24A, 24B) is about 2 mm to 20 mm.

As illustrated in FIGS. 2 and 3, in the fixing part 7 where the outer cover 2 and the absorbent assembly 3 are fixed, the outer cover 2 has a weak-functioning region WT in which the plurality of elastic members 24 are each divided into a plurality of pieces and the elastic members' elastic function is reduced. In the diaper 1A, each of the front panel 2A and the rear panel 2B has, in a region overlapping the absorbent assembly 3 and including the fixing part 7, a weak-functioning region WT in which the elastic function of the elastic members 24 is reduced. In further detail, the weak-functioning region WT is formed in a region where the front panel 2A or the rear panel 2B overlaps with the absorbent assembly 3, and more inward than the absorbent assembly 3's lateral-side end edges that extend along the Y direction. More specifically, in a state where the front panel 2A is spread out and stretched, the front panel 2A is fixed to the absorbent assembly 3 by an adhesive in the fixing part 7 which is located in the below-waist elasticized portion G2's central portion in the X direction; and the plurality of thread-form elastic members 24B in the below-waist elasticized portion G2 in a section overlapping the absorbent assembly 3 are each divided into a plurality of pieces. The finely divided elastic members 24B are in a state where they no longer exhibit hardly any contractile force, thus forming the weak-functioning region WT in the front panel 2A. Likewise, in a state where the rear panel 2B is spread out and stretched, the rear panel 2B is fixed to the absorbent assembly 3 by an adhesive in the fixing part 7 which is located in the below-waist elasticized portion G2's central portion in the X direction; and the plurality of thread-form elastic members 24B in the below-waist elasticized portion G2 in a section overlapping the absorbent assembly 3 are each divided into a plurality of pieces. The finely divided elastic members 24B are in a state where they no longer exhibit hardly any contractile force, thus forming the weak-functioning region WT in the rear panel 2B.

Further, in the outer cover 2, as illustrated in FIG. 3, in respective outer lateral sides of the weak-functioning region WT, lateral-side adhesion regions IT are formed in which the elastic members 24 are fixed between the outer sheet 22 and the inner sheet 23 by an adhesive 8; and in the vicinity of the respective side seals 4, side-seal adhesion regions OT are formed in which the elastic members 24 are fixed between the outer sheet 22 and the inner sheet 23 by an adhesive 8. Between the lateral-side adhesion region IT and the side-seal adhesion region OT, the elastic members 24 are not fixed between the outer sheet 22 and the inner sheet 23 by an adhesive. In the front panel 2A of the diaper 1A of the first embodiment, in respective outer lateral sides, in the X direction, of the weak-functioning region WT, lateral-side adhesion regions IT are formed in which the elastic members 24B forming the below-waist elasticized portion G2 are fixed between the outer sheet 22 and the inner sheet 23 by an adhesive 8; and in the vicinity of the respective side seals 4, side-seal adhesion regions OT are formed in which the elastic members 24A forming the waist elasticized portion G1 and the elastic members 24B forming the below-waist elasticized portion G2 are fixed between the outer sheet 22 and the inner sheet 23 by an adhesive 8; and between the lateral-side adhesion region IT and the side-seal adhesion region OT, the elastic members 24B forming the below-waist elasticized portion G2 are not fixed between the outer sheet 22 and the inner sheet 23. Like the front panel 2A, in the rear panel 2B of the diaper 1A, in respective outer lateral sides, in the X direction, of the weak-functioning region WT, lateral-side adhesion regions IT are formed in which the elastic members 24B forming the below-waist elasticized portion G2 are fixed between the outer sheet 22 and the inner sheet 23 by an adhesive 8; and in the vicinity of the respective side seals 4, side-seal adhesion regions OT are formed in which the elastic members 24A forming the waist elasticized portion G1 and the elastic members 24B forming the below-waist elasticized portion G2 are fixed between the outer sheet 22 and the inner sheet 23 by an adhesive 8; and between the lateral-side adhesion region IT and the side-seal adhesion region OT, the elastic members 24B forming the below-waist elasticized portion G2 are not fixed between the outer sheet 22 and the inner sheet 23.

As described above, the elastic members 24B forming the below-waist elasticized portion G2 are fixed between the sheets 22, 23 in the lateral-side adhesion regions IT and the side-seal adhesion regions OT, but are not fixed to either of the sheets 22, 23 in each region between the lateral-side adhesion region IT and the side-seal adhesion region OT.

It should be noted that, in both of the front panel 2A and the rear panel 2B, the elastic members 24A forming the waist elasticized portion G-1 are not fixed to either of the sheets 22, 23 in the region between the two side-seal adhesion regions OT, OT.

In the Y direction, each lateral-side adhesion region IT formed in the weak-functioning region WT's lateral side, which extends along the Y direction, is formed with substantially the same length as the length, in the Y direction, of the weak-functioning region WT in the below-waist elasticized portion G2. In the X direction, each lateral-side adhesion region IT is formed with a width of around 5 mm to 50 mm in a position more inward than the absorbent assembly 3's lateral-side end edge, which extends along the Y direction, and outward from the weak-functioning region WT's lateral-side end edge which extends along the Y direction.

In the Y direction, each side-seal adhesion region OT formed in the vicinity of the side seal 4 is forming with substantially the same length as the length, in the Y direction, of each of the front panel 2A and the rear panel 2B—i.e., is formed over the entire region in the Y direction so as to span the waist elasticized portion G1 and the below-waist elasticized portion G2. In the X direction, each side-seal adhesion region OT is formed with a width of around 5 mm to 50 mm in a position from the front panel 2A/rear panel 2B's lateral-side end edge, which extends along the Y direction, and including the side seal 4.

Figure 4:
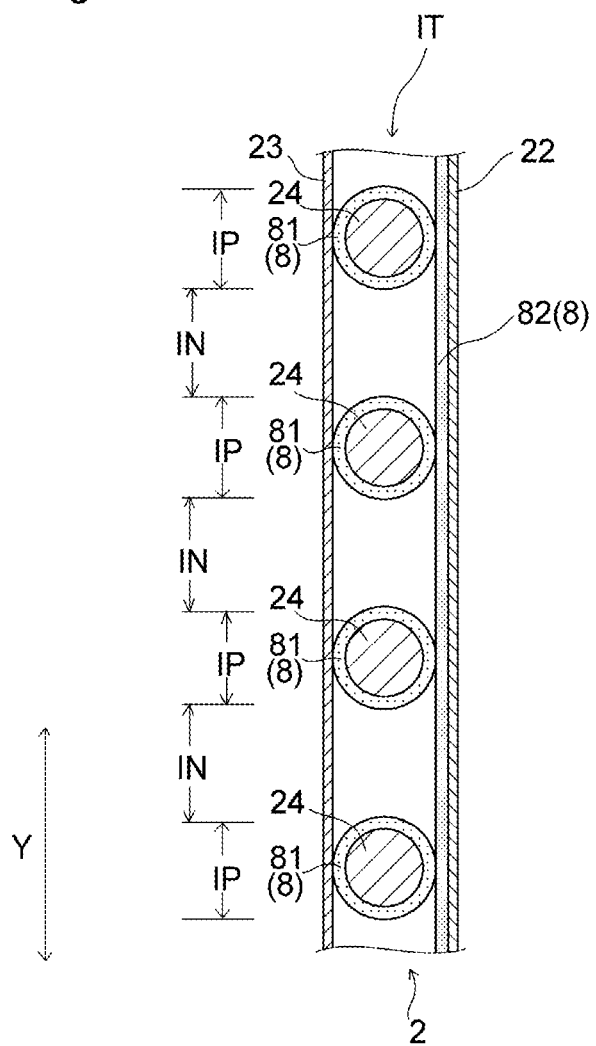
FIG. 4 is a cross-sectional view taken along line I-I of FIG. 3.

As illustrated in FIG. 3, in the diaper 1A, the adhesive 8 includes: an elastic-member-applied adhesive 81 that is applied to the peripheral surface of each elastic member 24, and that fixes each elastic member 24 between the outer sheet 22 and the inner sheet 23; and a sheet-applied adhesive 82 that is applied in a planar manner to at least one of the outer sheet 22 and the inner sheet 23 (the outer sheet 22 in the diaper 1A), and that fixes the elastic members 24 between the outer sheet 22 and the inner sheet 23. As illustrated in FIG. 4, in each lateral-side adhesion region IT in the outer lateral side of the weak-functioning region WT, the sheet-applied adhesive 82 is applied to the outer sheet 22 in a strip-like form that is long in the Y direction, and the elastic-member-applied adhesive 81 is applied to the peripheral surface of each elastic member 24B forming the below-waist elasticized portion G2. Further, as illustrated in FIG. 5, in each side-seal adhesion region OT in the vicinity of the side seal 4, the elastic-member-applied adhesive 81 is applied to the peripheral surface of each elastic member 24A forming the waist elasticized portion G1 and each elastic member 24B forming the below-waist elasticized portion G2.

Figure 5:
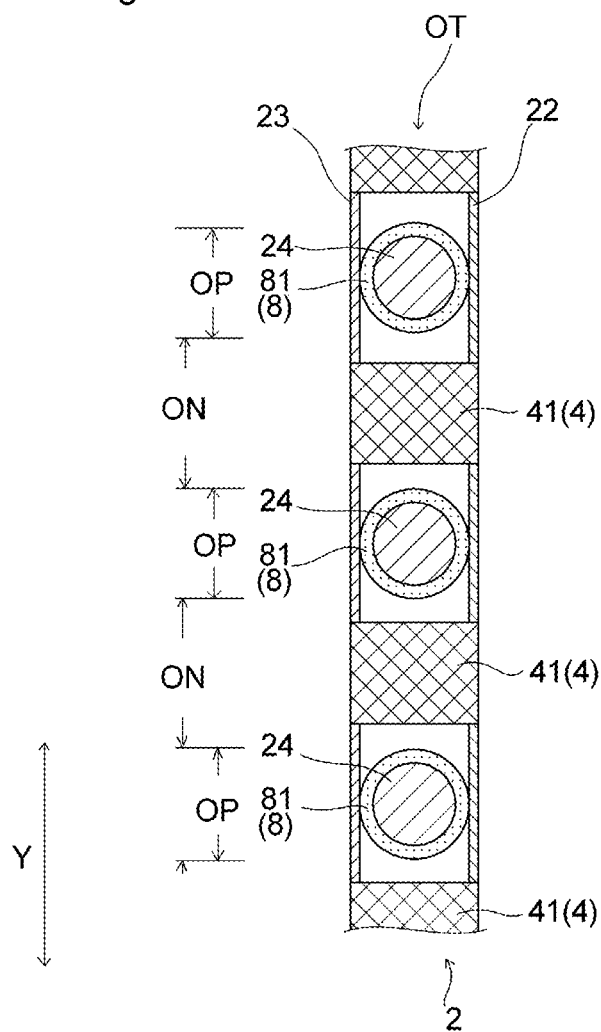
FIG. 5 is a cross-sectional view taken along line II-II of FIG. 3.

In the diaper 1A, because the front panel 2A and the rear panel 2B are formed as described above, the waist elasticized portion G1 in each of the front panel 2A and the rear panel 2B is formed so as to exhibit stretchability over the entire region between the side-seal adhesion regions OT, OT, whereas the below-waist elasticized portion G2 in each of the front panel 2A and the rear panel 2B is formed so as to exhibit stretchability over each region between the side-seal adhesion region OT and the lateral-side adhesion region IT, as illustrated in FIGS. 4 and 5. Stated differently, the below-waist elasticized portion G2 exhibits stretchability in sections more outward, in the X direction, than the vicinities of the absorbent assembly 3's lateral-side end edges extending along the Y direction, whereas the below-waist elasticized portion G2 hardly exhibits stretchability in the section overlapping the absorbent assembly 3; i.e., the elasticized portion is formed on the right and left of the diaper 1A in a divided state.

It should be noted that, in the diaper 1A of the first embodiment, the elastic members 24B which are each divided into a plurality of pieces in the weak-functioning region WT are fixed between the outer sheet 22 and the inner sheet 23 by the adhesive 8. More specifically, in the front panel 2A, the plurality of elastic members 24B are each divided into a plurality of pieces in the weak-functioning region WT which is located in the below-waist elasticized portion G2's central portion in the X direction and between the two lateral-side adhesion regions IT, IT, and each of the finely divided elastic members 24B is fixed between the outer sheet 22 and the inner sheet 23 by an adhesive 8. Note that, as described above, the finely divided elastic members 24B are in a state where they no longer exhibit hardly any contractile force. As in the front panel 2A, in the rear panel 2B, the plurality of elastic members 24B are each divided into a plurality of pieces in the weak-functioning region WT which is located in the below-waist elasticized portion G2's central portion in the X direction and between the two lateral-side adhesion regions IT, IT, and each of the finely divided elastic members 24B is fixed between the outer sheet 22 and the inner sheet 23 by an adhesive 8.

As illustrated in FIGS. 4 and 5, in each of the lateral-side adhesion regions IT and each of the side-seal adhesion regions OT, the basis weight of the adhesive 8 in each section IP, OP where the elastic member 24 is arranged is higher than the basis weight of the adhesive 8 in each section IN, ON between adjacent elastic members 24, 24, and sections having a high basis weight and sections having a low basis weight in adhesive 8 alternate repeatedly in the Y direction of the diaper 1A. That is, in the lateral-side adhesion region IT, sections IP where the elastic members 24 are arranged and sections IN which are located between respective pairs of adjacent elastic members 24, 24 alternate repeatedly in the Y direction; the elastic-member-applied adhesive 81 and the sheet-applied adhesive 82 are arranged in each section IP where the elastic member 24 is arranged, and substantially only the sheet-applied adhesive 82 is arranged in each section IN which is located between each pair of adjacent elastic members 24, 24. In the side-seal adhesion region OT, sections OP where the elastic members 24 are arranged and sections ON which are located between respective pairs of adjacent elastic members 24, 24 alternate repeatedly in the Y direction; the elastic-member-applied adhesive 81 is arranged only in each section OP where the elastic member 24 is arranged, and substantially no adhesive 8 is arranged in each section ON which is located between each pair of adjacent elastic members 24, 24.

From the viewpoint of preventing the elastic members 24 from falling out, the basis weight of the adhesive 8 (elastic-member-applied adhesive 81 and sheet-applied adhesive 82) in each section IP, of the lateral-side adhesion region IT in the front panel 2A, where the elastic member 24 (24B) is arranged is preferably 11 g/m$^2$ or greater, more preferably 18 g/m$^2$ or greater, and preferably 90 g/m$^2$ or less, more preferably 70 g/m$^2$ or less, and more specifically, preferably from 11 g/m$^2$ to 90 g/m$^2$ inclusive, more preferably from 18 g/m$^2$ to 70 g/m$^2$ inclusive. The rear panel 2B is the same as the front panel 2A.

From the viewpoint of preventing the elastic members 24 from falling out, the basis weight of the adhesive 8 (substantially only the sheet-applied adhesive 82) in each section IN, of the lateral-side adhesion region IT in the front panel 2A, which is located between each pair of adjacent elastic members 24 (24B) is preferably 1 g/m$^2$ or greater, more preferably 3 g/m$^2$ or greater, and preferably 30 g/m$^2$ or less, more preferably 20 g/m$^2$ or less, and more specifically, preferably from 1 g/m$^2$ to 30 g/m$^2$ inclusive, more preferably from 3 g/m$^2$ to 20 g/m$^2$ inclusive. The rear panel 2B is the same as the front panel 2A.

From the viewpoint of preventing the elastic members 24 from falling out, the basis weight of the adhesive 8 (substantially only the elastic-member-applied adhesive 81) in each section OP, of the side-seal adhesion region OT in the front panel 2A, where the elastic member 24 (24A, 24B) is arranged is preferably 10 g/m$^2$ or greater, more preferably 15 g/m$^2$ or greater, and preferably 60 g/m$^2$ or less, more preferably 50 g/m$^2$ or less, and more specifically, preferably from 10 g/m$^2$ to 60 g/m$^2$ inclusive, more preferably from 15 g/m$^2$ to 50 g/m$^2$ inclusive. The rear panel 2B is the same as the front panel 2A.

From the viewpoint of improving softness, the smaller the basis weight of the adhesive 8 (substantially no adhesive) in each section ON, of the side-seal adhesion region OT in the front panel 2A, which is located between each pair of adjacent elastic members 24 (24A, 24B) is, the more preferable, and the basis weight is preferably 0 g/m$^2$. The rear panel 2B is the same as the front panel 2A.

The basis weight of the adhesive is the weight of the adhesive included in a unit area in a predetermined section in the lateral-side adhesion region IT or the side-seal adhesion region OT, and can be measured as follows.

First, the side seals 4 of the diaper 1A are torn open, and the absorbent assembly 3 fixed by the fixing part 7 is removed, to obtain the front panel 2A and the rear panel 2B. Next, the side-seal adhesion region OT (having a length L1 in the X direction where the adhesive is applied) is cut out from the obtained front panel 2A or rear panel 2B by cutting the front panel 2A or the rear panel 2B at a position that gives a 10-mm width from the panel's lateral-side end edge, which extends along the Y direction, while including the side seal 4. Also, the lateral-side adhesion region IT having a width of 10 mm is cut out from the obtained front panel 2A or rear panel 2B by: cutting out the below-waist elasticized portion G2; and cutting the below-waist elasticized portion G2 along the Y direction at the position of the weak-functioning region WT's lateral-side end edge, which extends along the Y direction, and at a position that is located 10 mm outward in the X direction from the lateral-side end edge.

Next, from the cut-out side-seal adhesion region OT, a plurality of sections OP where the respective elastic members 24 (24A, 24B) are arranged are cut out by cutting side-seal adhesion region OT in the X direction. At this time, the area of the sections OP is calculated from the width L1 and the number of cut-out elastic members 24, by fixing the length, in the Y direction, where the elastic-member-applied adhesive 81 is applied at 1 mm. Also, parts between respective pairs of adjacent elastic members 24 (24A, 24B) that are created at the time of cutting out the sections OP are considered the sections ON between respective pairs of adjacent elastic members 24 (24A, 24B). The sections OP where the respective elastic members 24 (24A, 24B) are arranged are in a state where the elastic members 24 (24A, 24B) are fixed between the outer sheet 22 and the inner sheet 23 by the adhesive 8. Next, the weight W1 of the cut-out sections OP—where the respective elastic members 24 (24A, 24B) are arranged—is measured, and then, the sections OP are cleaned with an organic solvent (chloroform, toluene, etc.) that can dissolve the adhesive, to wash out the adhesive 8. Then, the elastic members 24 (24A, 24B), the outer sheet 22, and the inner sheet 23 are taken out and the organic solvent is vaporized from the elastic members 24 (24A, 24B), the outer sheet 22, and the inner sheet 23, and then, the total weight W2 of the elastic members and the sheets is measured. The difference (W2−W1) between the weight W2 and weight W1 is found as the weight of the adhesive 8 in the aforementioned sections OP. By dividing this weight by the area of the aforementioned sections OP, the basis weight (g/m$^2$) of the adhesive 8 in the section OP, of the side-seal adhesion region OT, where the elastic member 24 (24A, 24B) is arranged is calculated. It should be noted that the basis weight of the adhesive 8 in the section ON which is located between adjacent elastic members 24 (24A, 24B) is calculated in the same manner as the basis weight of the adhesive 8 in the section OP where the elastic member 24 (24A, 24B) is arranged—i.e., by dissolving the adhesive by using an organic solvent, finding the weight of the adhesive 8 from the weight difference before and after the dissolution, and dividing the weight of the adhesive 8 by the area of the section(s) ON.

In the same manner, the basis weight of the adhesive 8 (the total of the elastic-member-applied adhesive 81 and the sheet-applied adhesive 82) in the section IP where the elastic member 24 (24B) is arranged, and the basis weight of the adhesive 8 (sheet-applied adhesive 82) in the section IN which is between adjacent elastic members 24 (24B) are calculated from the cut-out lateral-side adhesion region IT.

It should be noted that, although the Y-direction length where the elastic-member-applied adhesive 81 is applied is fixed to 1 mm because the elastic member 24 (24A, 24B) is a thread-form elastic member, the Y-direction length where the elastic-member-applied adhesive 81 is applied may actually be measured with a magnifying glass etc. in cases where the elastic member is thicker than 1 mm.

In the diaper 1A of the first embodiment, the basis weight of the adhesive 8 in the section IP, of the lateral-side adhesion region IT, where the elastic member 24 is arranged is greater than the basis weight of the adhesive 8 in the section OP, of the side-seal adhesion region OT, where the elastic member 24 is arranged.

Also, in the diaper 1A of the first embodiment, the basis weight of the adhesive 8 in the section IN, of the lateral-side adhesion region IT, which is located between adjacent elastic members 24, 24 is greater than the basis weight of the adhesive 8 in the section ON, of the side-seal adhesion region OT, which is between adjacent elastic members 24, 24.

In the diaper 1A of the first embodiment, as illustrated in FIGS. 1, 3, and 5, each of the lateral side edge portions 2a, 2a of the front panel 2A are placed flat against the respective lateral side edge portions 2b, 2b of the rear panel 2B in gassho-style (like two hands joined in prayer), and the panels' lateral side edge portions are bonded by a multitude of sealed portions 41, which are arranged intermittently in the Y direction, at a position more inward in the X direction than the front panel 2A's lateral-side end edge, which extends along the Y direction, and the rear panel 2B's lateral-side end edge, which extends along the Y direction. Each of the side seals 4 is formed by the multitude of sealed portions 41, which are arranged intermittently in the Y direction. In the first embodiment, from the viewpoint of improving softness, the sealed portions 41 are arranged between adjacent elastic members 24 (24A, 24B) so that the sealed portions 41 do not overlap the elastic members 24 (24A, 24B) to the extent possible, as illustrated in FIG. 5, and are formed along the X direction in parallel to one another. The side seal 4 is formed within the side-seal adhesion region OT.

There is no particular limitation to the method for manufacturing the diaper 1A of the first embodiment, and the diaper can be manufactured according to any discretionary method. A preferred example of a method for manufacturing the diaper 1A of the first embodiment is described below with reference to FIGS. 6 and 7.

Figure 6:
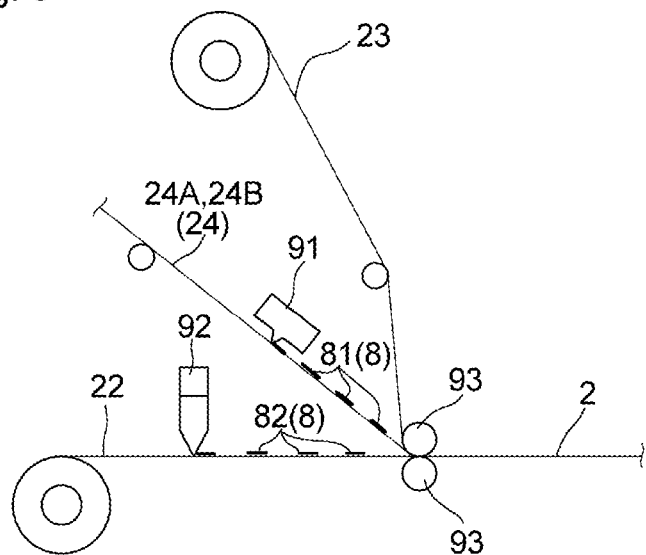
FIG. 6 is a side view schematically illustrating an example of the first half of processes for manufacturing the pull-on disposable diaper illustrated in FIG. 1.
Figure 7:
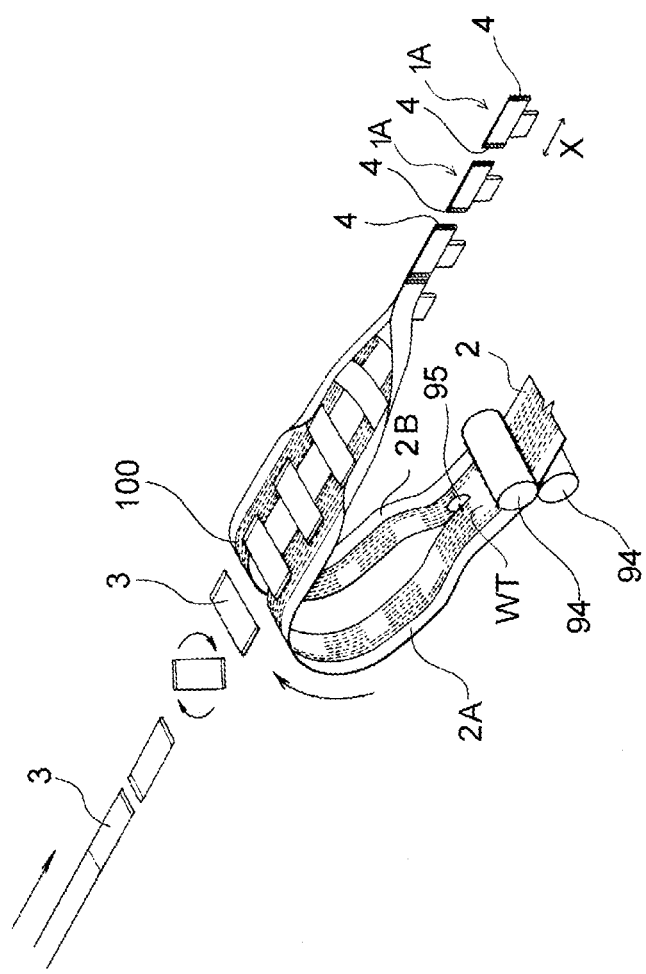
FIG. 7 is a perspective view schematically illustrating an example of the second half of processes for manufacturing the pull-on disposable diaper illustrated in FIG. 1.

The method for manufacturing the diaper 1A of the present embodiment is a pull-on disposable diaper manufacturing method according to the so-called cross-flow system, as illustrated in FIGS. 6 and 7.

First, as illustrated in FIG. 6, a plurality of elastic members 24A for forming the waist elasticized portion G1 and a plurality of elastic members 24B for forming the below-waist elasticized portion G2 are arranged between a continuous outer sheet 22, which is continuously supplied from an original textile roll (not illustrated), and a continuous inner sheet 23, which is continuously supplied from an original textile roll (not illustrated), the elastic members 24A and the elastic members 24B being in a stretched state where they are stretched to a predetermined extension rate. At this time, in the present embodiment, the plurality of elastic members 24A for forming the waist elasticized portion G1 and the plurality of elastic members 24B for forming the below-waist elasticized portion G2 are passed through grooves of a comb gun 91 for applying an adhesive 8, thus applying an elastic-member-applied adhesive 81 onto each elastic member 24 (24A, 24B) at the bottom of each groove. The comb gun 91 intermittently applies the elastic-member-applied adhesive 81 to the elastic members 24A for forming the waist elasticized portion G1 in each region including a section corresponding to the side seal 4 (i.e., in each region wider than the side seal 4's length in the transporting direction). The comb gun 91 intermittently applies the elastic-member-applied adhesive 81 to the elastic members 24B for forming the below-waist elasticized portion G2 in each region including a section corresponding to the side seal 4 (i.e., in each region wider than the side seal 4's length in the transporting direction) and in each region including a section corresponding to the weak-functioning region WT (i.e., in each region wider than the weak-functioning region WT's length in the transporting direction).

Further, as illustrated in FIG. 6, before superposing the continuous outer sheet 22 and the continuous inner sheet 23 on top of one another, a sheet-applied adhesive 82 is applied to one opposing surface of the sheets 22 or 23, or to opposing surfaces of both the sheets 22, 23, with a coater 92. More specifically, the coater 92 applies the sheet-applied adhesive 82 in a planar manner and intermittently in a direction orthogonal to the transporting direction in each section corresponding to an area located outward, in the transporting direction, from each lateral-side end edge of the weak-functioning region WT in the below-waist elasticized portion G2.

Then, as illustrated in FIG. 6, the continuous outer sheet 22 and the continuous inner sheet 23—which have the plurality of elastic members 24A for forming the waist elasticized portion G1 and the plurality of elastic members 24B for forming the below-waist elasticized portion G2 sandwiched therebetween in a stretched state—are fed between a pair of nip rollers 93, 93 and are pressurized therebetween, thus forming a continuous outer cover 2 in which a plurality of elastic members 24 are arranged in a stretched state between the continuous sheets 22, 23.

Then, in the present embodiment, as illustrated in FIG. 7, by using elastic-member dividing means 94, 94, the plurality of elastic members 24B for forming the below-waist elasticized portion G2 are pressed in areas corresponding to the positions where the respective absorbent assemblies 3 are to be arranged, as described below, thereby forming weak-functioning regions WT in the below-waist elasticized portion G2 by dividing each elastic member into a plurality of pieces so that the elastic members do not exhibit contractile functions. An example of the elastic-member dividing means 94, 94 is an elastic-member dividing unit used in a composite-elasticized-member manufacturing method disclosed in JP 2002-253605A.

Next, as illustrated in FIG. 7, the continuous outer cover, in which the elastic members 24B have been divided into a plurality of pieces, is split into two outer covers 2 by a splitting means 95. The two continuous outer covers 2 created by splitting are each used as the front panel 2A and the rear panel 2B.

Any one of various known cutting devices capable of continuously cutting a sheet may be used as the splitting means 95. For example, it is possible to use a device having a cutter blade on the upstream side of the sheet transporting direction, a cylindrical or disk-shaped cutter having an annular blade on the peripheral surface or peripheral edge thereof, a laser cutter, or a high-pressure water jet cutter.

An adhesive, such as a hot-melt adhesive, is applied in advance to each absorbent assembly 3 manufactured in a separate process, and then, as illustrated in FIG. 7, each absorbent assembly 3 is rotated by 90 degrees, and the absorbent assemblies are intermittently supplied and fixed onto the inner sheet 23 of each of the continuous front panel 2A and the continuous rear panel 2B, thereby forming a continuous strip 100 of diapers 1A. Then, as illustrated in FIG. 7, the continuous front panel 2A and the continuous rear panel 2B are superposed on one another such that the panels' lateral sides extending along the transporting direction overlap one another. Then, side seals 4 are formed intermittently, and thereafter, the continuous strip is cut at the side seals 4, to thereby continuously form diapers 1A each having side seals 4.

The effects of using the aforementioned diaper 1A of the first embodiment of the invention are described below.

As illustrated in FIG. 3, in the below-waist elasticized portion G2, the diaper 1A has, in a fixing part 7 where the outer cover 2 and the absorbent assembly 3 are fixed, a weak-functioning region WT in which the elastic function of the elastic members 24B for forming the below-waist elasticized portion G2 is reduced. Thus, creases are less likely to be created in the absorbent member 33 by the elastic members 24B, and outer appearance is improved. Further, as illustrated in FIG. 3, in the waist elasticized portion G1 of the diaper 1A, between the side-seal adhesion regions OT, the elastic members 24A for forming the waist elasticized portion G1 are not fixed between the outer sheet 22 and the inner sheet 23 by an adhesive; and in the below-waist elasticized portion G2, between the lateral-side adhesion region IT—which is located in the outer lateral side of the weak-functioning region WT—and the side-seal adhesion region OT, the elastic members 24B for forming the below-waist elasticized portion G2 are not fixed between the outer sheet 22 and the inner sheet 23 by an adhesive. Thus, the texture of the diaper 1A is improved. Further, as illustrated in FIGS. 3 and 4, in each lateral-side adhesion region IT of the diaper 1A, sections IP where the elastic members 24 are arranged and sections IN between respective pairs of adjacent elastic members 24, 24 alternate repeatedly in the Y direction. Also, as illustrated in FIGS. 3 and 5, in each side-seal adhesion region OT of the diaper 1A, sections OP where the elastic members 24 are arranged and sections ON between respective pairs of adjacent elastic members 24, 24 alternate repeatedly in the Y direction. Thus, sections where the adhesive is applied are less likely to become stiff and the texture of the diaper 1A is improved, and also, the elastic members 24 are less likely to fall out.

More specifically, in the diaper 1A, the basis weight of the adhesive 8 in the section IP, of the lateral-side adhesion region IT, where the elastic member 24 is arranged is greater than the basis weight of the adhesive 8 in the section OP, of the side-seal adhesion region OT, where the elastic member 24 is arranged. Also, the basis weight of the adhesive 8 in the section IN, of the lateral-side adhesion region IT, which is located between adjacent elastic members 24, 24 is greater than the basis weight of the adhesive 8 in the section ON, in the side-seal adhesion region OT, which is located between adjacent elastic members 24, 24. Thus, the elastic members 24 in the diaper 1A are less likely to fall out in the lateral-side adhesion regions IT where no side seal 4 is formed.

In the aforementioned embodiment regarding the method for manufacturing the diaper 1A, the elastic-member-applied adhesive 81 is applied, by a comb gun 91, to the elastic members 24B for forming the below-waist elasticized portion G2 in each region including a section corresponding to the weak-functioning region WT (i.e., in each region wider than the weak-functioning region WT's length in the transporting direction). Thus, at the time of forming a weak-functioning region WT in the below-waist elasticized portion G2 by pressing the plurality of elastic members 24B, which are for forming the below-waist elasticized portion G2, with the elastic-member dividing means 94 and dividing the elastic members into a plurality of pieces, the force for cutting the elastic members is likely to be enhanced, and cutting failure is less likely to occur. Air permeability is also improved in this diaper 1A, which has a weak-functioning region WT formed as above.

Further, in the diaper 1A, the elastic members 24B—which have each been divided into a plurality of pieces in the weak-functioning region WT—are fixed between the outer sheet 22 and the inner sheet 23 by the adhesive 8. Thus, the outer appearance of the diaper 1A is improved. Although the divided elastic members 24B no longer exhibit any contractile function, they are fixed between the outer sheet 22 and the inner sheet 23 along the X direction intermittently and in parallel to one another, and so, the user is likely to think that the diaper still has contractile functions around the below-waist, thus enhancing the user's sense of security.

Next, disposable diapers according to second to fifth embodiments of the invention are described. In the disposable diapers 1B to 1E of the second to fifth embodiments, the structure of the lateral-side adhesion region IT or the structure of the side-seal adhesion region OT is different from that of the diaper 1A of the first embodiment. The following description regarding the diapers 1B to 1E of the second to fifth embodiments mainly focuses on features that are different from those in the diaper 1A of the first embodiment, and features that are the same are accompanied by the same reference signs and explanation thereof is omitted. The explanation on the diaper 1A of the first embodiment applies as appropriate to features that are not particularly explained.

The rear panel 2B is similar to the front panel 2A, and so, the following description mainly focuses on the front panel 2A.

The structure of the lateral-side adhesion region IT and the structure of the side-seal adhesion region OT of the diaper 1B of the second embodiment are described in detail.

Figure 8:
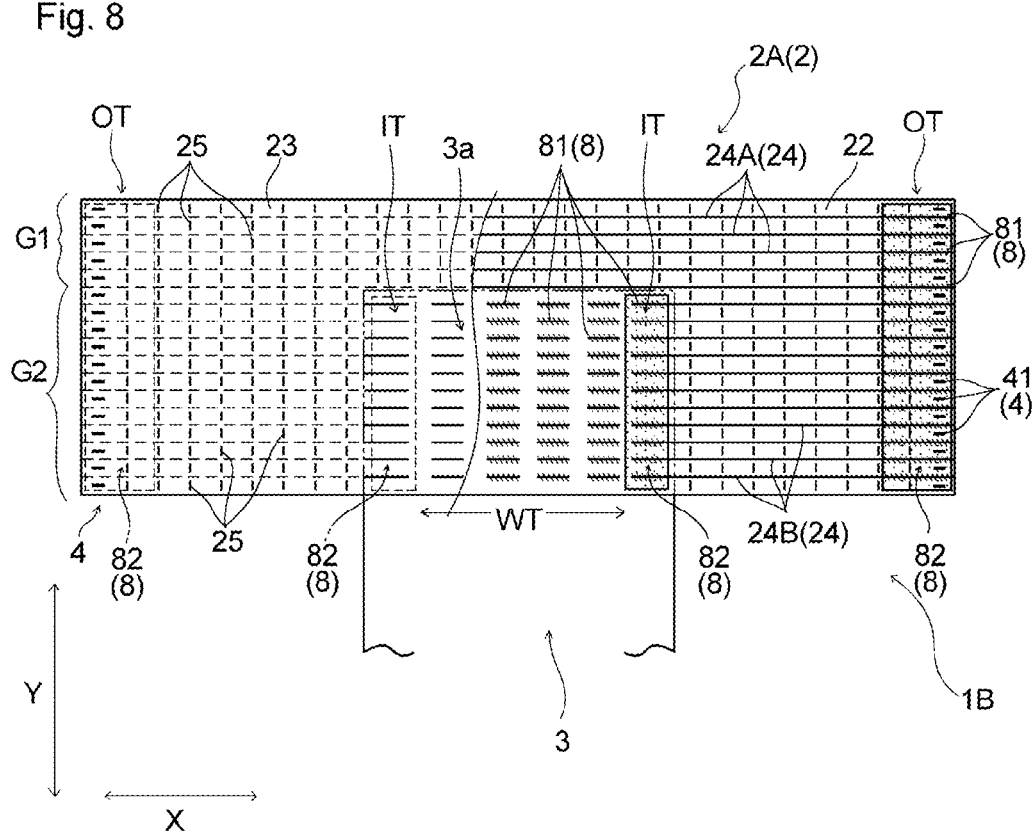
FIG. 8 is a partially cutaway enlarged view (corresponding to FIG. 3) of a front portion side, in a stretched state, of a pull-on disposable diaper according to a second embodiment of the invention as viewed from the diaper's inner surface side.

As illustrated in FIG. 8, as in the diaper 1A, in each lateral-side adhesion region IT of the weak-functioning region WT of the diaper 1B, the sheet-applied adhesive 82 is applied to the outer sheet 22 in a strip-like form that is long in the Y direction, and the elastic-member-applied adhesive 81 is applied to the peripheral surface of each elastic member 24B forming the below-waist elasticized portion G2.

Further, as illustrated in FIG. 8, in each side-seal adhesion region OT in the vicinity of each side seal 4 of the diaper 1B, the sheet-applied adhesive 82 is applied to the outer sheet 22 in a strip-like form that is long in the Y direction over the entire region in the Y direction, and the elastic-member-applied adhesive 81 is applied to the peripheral surface of each elastic member 24A forming the waist elasticized portion G1 and each elastic member 24B forming the below-waist elasticized portion G2.

In the diaper 1B, the basis weight of the adhesive 8 in the section IP, of the lateral-side adhesion region IT, where the elastic member 24 is arranged is the same as the basis weight of the adhesive 8 in the section OP, of the side-seal adhesion region OT, where the elastic member 24 is arranged, and the basis weight of the adhesive 8 in the section IN, of the lateral-side adhesion region IT, which is located between adjacent elastic members 24, 24 is the same as the basis weight of the adhesive 8 in the section ON, of the side-seal adhesion region OT, which is located between adjacent elastic members 24, 24. Thus, the diaper 1B achieves the same effects as the diaper 1A of the first embodiment.

Next, the structure of the lateral-side adhesion region IT and the structure of the side-seal adhesion region OT of the diaper 1C of the third embodiment are described in detail.

Figure 9:
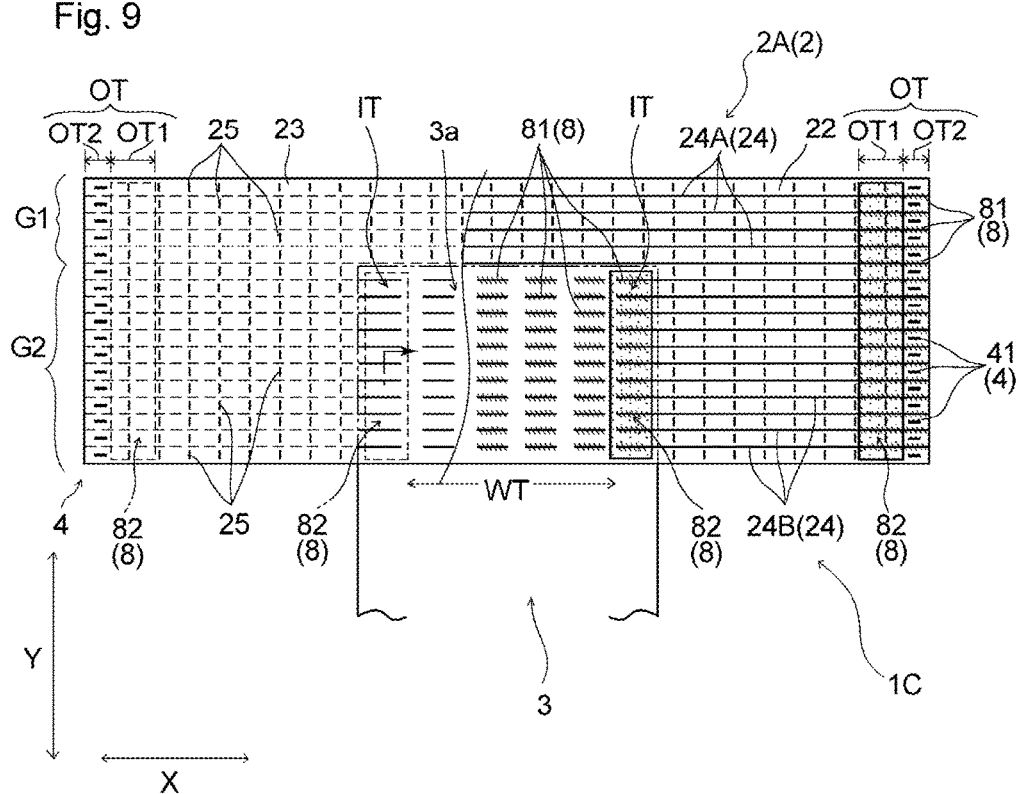
FIG. 9 is a partially cutaway enlarged view (corresponding to FIG. 3) of a front portion side, in a stretched state, of a pull-on disposable diaper according to a third embodiment of the invention as viewed from the diaper's inner surface side.

As illustrated in FIG. 9, as in the diaper 1A, in each lateral-side adhesion region IT of the weak-functioning region WT of the diaper 1C, the sheet-applied adhesive 82 is applied to the outer sheet 22 in a strip-like form that is long in the Y direction, and the elastic-member-applied adhesive 81 is applied to the peripheral surface of each elastic member 24B forming the below-waist elasticized portion G2.

As illustrated in FIG. 9, in the side-seal adhesion region OT in the vicinity of each side seal 4 of the diaper 1C, the side-seal adhesion region OT consists of: a side-seal inner adhesion region OT1 located more inward in the width direction (X direction) than the side seal 4; and a side-seal outer adhesion region OT2 located more outward in the width direction (X direction) than the side-seal inner adhesion region OT1.

In the side-seal inner adhesion region OT1 of the diaper 1C, as illustrated in FIG. 9, the sheet-applied adhesive 82 is applied to the outer sheet 22 in a strip-like form that is long in the Y direction over the entire region in the Y direction, and the elastic-member-applied adhesive 81 is applied to the peripheral surface of each elastic member 24A forming the waist elasticized portion G1 and each elastic member 24B forming the below-waist elasticized portion G2.

In the side-seal outer adhesion region OT2 of the diaper 1C, as illustrated in FIG. 9, only the elastic-member-applied adhesive 81 is applied to the peripheral surface of each elastic member 24A forming the waist elasticized portion G1 and each elastic member 24B forming the below-waist elasticized portion G2.

In the diaper 1C, the basis weight of the adhesive 8 in the section IP, of the lateral-side adhesion region IT, where the elastic member 24 is arranged is the same as the basis weight of the adhesive 8 in the section OP, of the side-seal inner adhesion region OT1 constituting the side-seal adhesion region OT, where the elastic member 24 is arranged, and the basis weight of the adhesive 8 in the section IP, of the lateral-side adhesion region IT, where the elastic member 24 is arranged is greater than the basis weight of the adhesive 8 in the section OP, of the side-seal outer adhesion region OT2 constituting the side-seal adhesion region OT, where the elastic member 24 is arranged. Further, the basis weight of the adhesive 8 in the section IN, of the lateral-side adhesion region IT, which is located between adjacent elastic members 24, 24 is the same as the basis weight of the adhesive 8 in the section ON, of the side-seal inner adhesion region OT1 constituting the side-seal adhesion region OT, which is located between adjacent elastic members 24, 24, and the basis weight of the adhesive 8 in the section IN, of the lateral-side adhesion region IT, which is located between adjacent elastic members 24, 24 is greater than the basis weight of the adhesive 8 in the section ON, of the side-seal outer adhesion region OT2 constituting the side-seal adhesion region OT, which is located between adjacent elastic members 24, 24. Thus, the diaper 1C achieves the same effects as the diaper 1A of the first embodiment.

The structure of the lateral-side adhesion region IT and the structure of the side-seal adhesion region OT of the diaper 1D of the fourth embodiment are described in detail.

Figure 10:
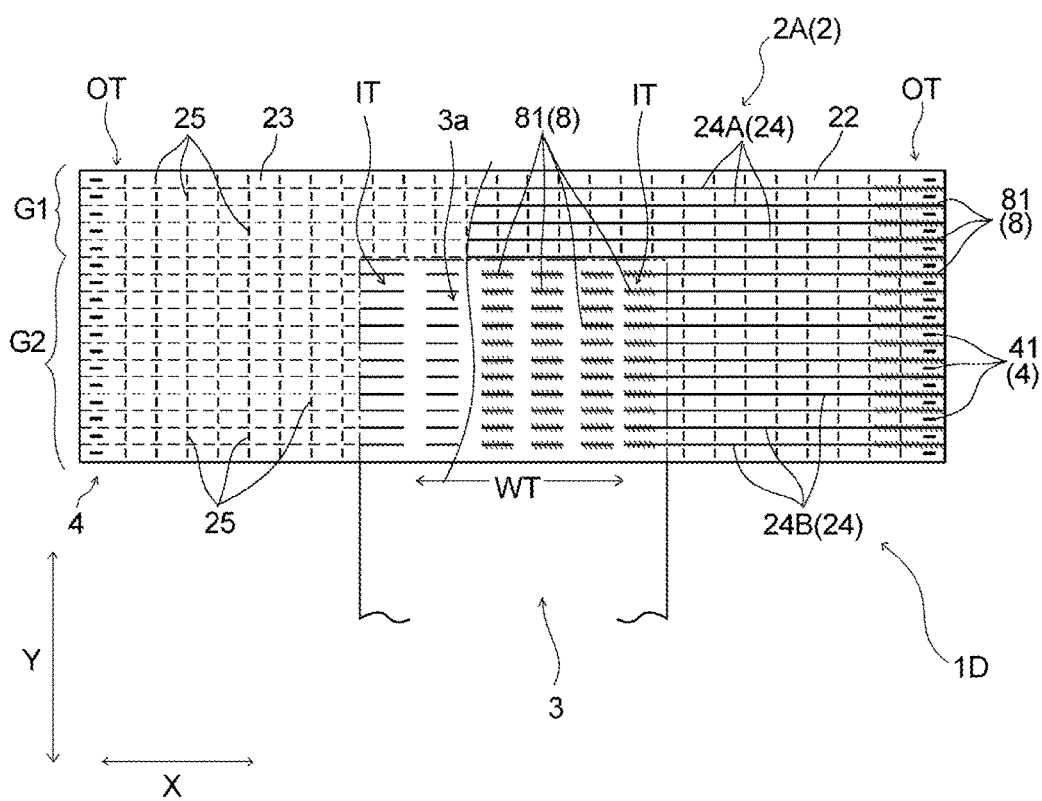
FIG. 10 is a partially cutaway enlarged view (corresponding to FIG. 3) of a front portion side, in a stretched state, of a pull-on disposable diaper according to a fourth embodiment of the invention as viewed from the diaper's inner surface side.

As illustrated in FIG. 10, in each lateral-side adhesion region IT of the weak-functioning region WT of the diaper 1D, only the elastic-member-applied adhesive 81 is applied to the peripheral surface of each elastic member 24B forming the below-waist elasticized portion G2.

Further, as illustrated in FIG. 10, as in the diaper 1A, in each side-seal adhesion region OT in the vicinity of each side seal 4 of the diaper 1D, only the elastic-member-applied adhesive 81 is applied to the peripheral surface of each elastic member 24A forming the waist elasticized portion G1 and each elastic member 24B forming the below-waist elasticized portion G2.

In the diaper 1D, the basis weight of the adhesive 8 in the section IP, of the lateral-side adhesion region IT, where the elastic member 24 is arranged is the same as the basis weight of the adhesive 8 in the section OP, of the side-seal adhesion region OT, where the elastic member 24 is arranged, and the basis weight of the adhesive 8 in the section IN, of the lateral-side adhesion region IT, which is located between adjacent elastic members 24, 24 is the same as the basis weight of the adhesive 8 in the section ON, of the side-seal adhesion region OT, which is located between adjacent elastic members 24, 24. The diaper 1D is improved in softness because the inner sheet 23 and the outer sheet 22 are bonded together only in regions where the elastic members 24 are arranged.

Next, the structure of the lateral-side adhesion region IT and the structure of the side-seal adhesion region OT of the diaper 1E of the fifth embodiment are described in detail.

Figure 11:
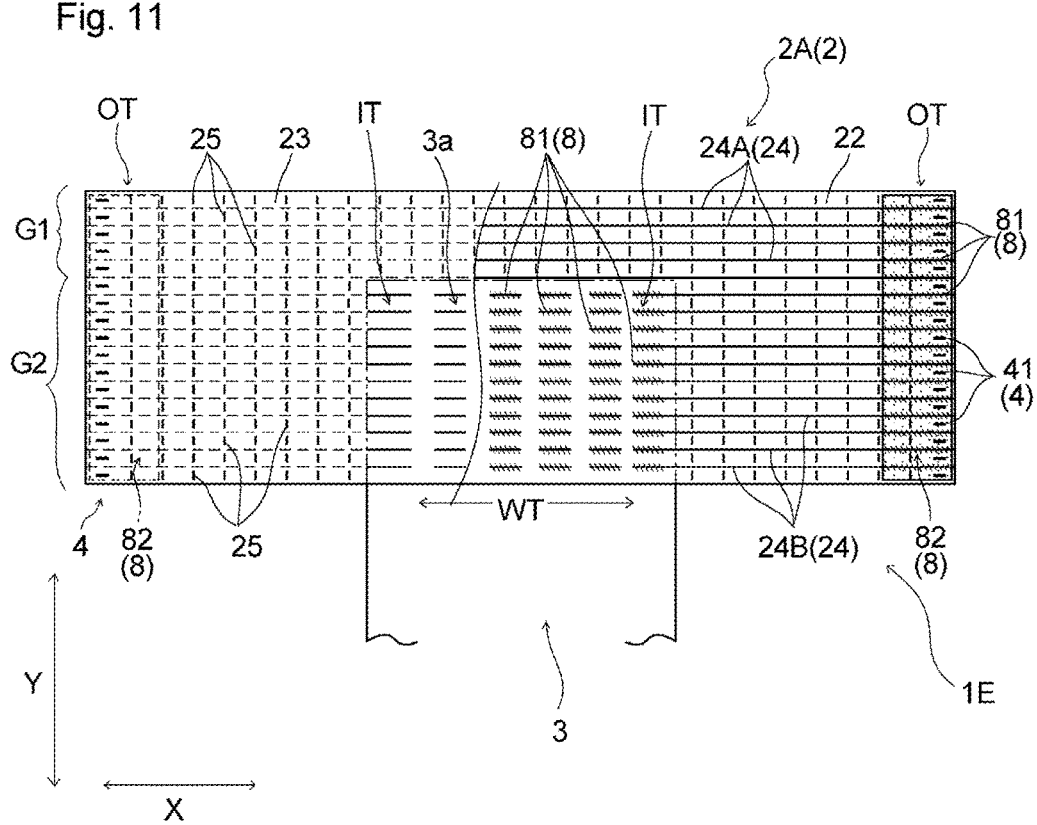
FIG. 11 is a partially cutaway enlarged view (corresponding to FIG. 3) of a front portion side, in a stretched state, of a pull-on disposable diaper according to a fifth embodiment of the invention as viewed from the diaper's inner surface side.

As illustrated in FIG. 11, in each lateral-side adhesion region IT of the weak-functioning region WT of the diaper 1E, only the elastic-member-applied adhesive 81 is applied to the peripheral surface of each elastic member 24B forming the below-waist elasticized portion G2.

Further, as illustrated in FIG. 11, in each side-seal adhesion region OT in the vicinity of each side seal 4 of the diaper 1E, the sheet-applied adhesive 82 is applied to the outer sheet 22 in a strip-like form that is long in the Y direction over the entire region in the Y direction, and the elastic-member-applied adhesive 81 is applied to the peripheral surface of each elastic member 24A forming the waist elasticized portion G1 and each elastic member 24B funning the below-waist elasticized portion G2.

In the diaper 1E, the basis weight of the adhesive 8 in the section IP, of the lateral-side adhesion region IT, where the elastic member 24 is arranged is smaller than the basis weight of the adhesive 8 in the section OP, of the side-seal adhesion region OT, where the elastic member 24 is arranged, and the basis weight of the adhesive 8 in a section IN, of the lateral-side adhesion region IT, which is located between adjacent elastic members 24, 24 is smaller than the basis weight of the adhesive 8 of a section ON, in the side-seal adhesion region OT, which is located between adjacent elastic members 24, 24. Thus, the diaper 1E achieves the same effects as the diaper 1A of the first embodiment.

The present invention has been described above according to preferred first to fifth embodiments thereof, but the invention is not limited to the aforementioned first to fifth embodiments, and may be modified as appropriate.

For example, the diapers 1A to 1E of the foregoing first to fifth embodiments are pull-on disposable diapers in which the outer cover 2 is separated between the wearer's rear side (rear panel 2B) and the wearer's front side (front panel 2A), as illustrated in FIG. 1 and FIGS. 8 to 11. The diaper, however, may be a pull-on disposable diaper in which a single outer cover 2 is formed in a shape that is narrowed inwardly at the central portion in the Y direction.

Figure 12:
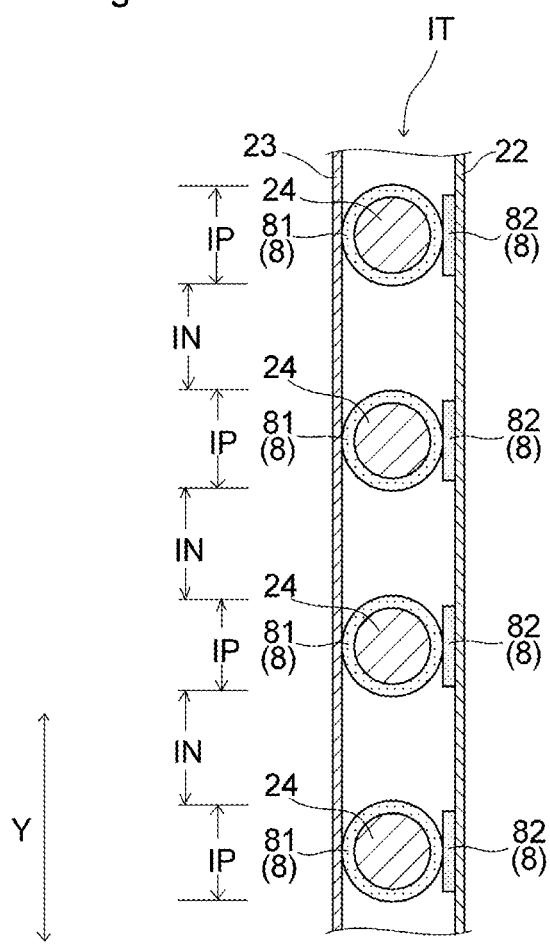
FIG. 12 is a cross-sectional view (corresponding to FIG. 4) of a lateral-side adhesion region of a pull-on disposable diaper according to another embodiment of the invention.

Further, in the diapers 1A to 1C, and 1E of the foregoing first to third, and fifth embodiments, the sheet-applied adhesive 82 constituting each lateral-side adhesion region IT in the outer lateral side of the weak-functioning region WT, or the sheet-applied adhesive 82 constituting the side-seal adhesion region OT in the vicinity of each side seal 4, is applied continuously to the outer sheet 22 in a strip-like form that is long in the Y direction, as illustrated in FIG. 4 and FIGS. 8 to 11. The sheet-applied adhesive 82, however, may be applied intermittently in the Y direction so as to correspond to positions where the elastic members 24B forming the below-waist elasticized portion G2 are arranged, or correspond to positions where the elastic members 24A forming the waist elasticized portion G1 are arranged, as illustrated in FIG. 12. By applying the adhesive intermittently in this way, the sections where the adhesive is applied are less likely to become stiff, and the texture of the diaper 1A-1E is further improved.

Further, in the diaper 1A of the foregoing first embodiment, the outer sheet 22 and the inner sheet 23 constituting the front panel 2A/rear panel 2B are formed with the same shape and same size, as illustrated in FIG. 2. The sheets, however, do not have to have the same shape and same size, and at least one of the outer sheet 22 and the inner sheet 23 may have an extension portion that extends outward from the peripheral edge of the waist opening 5, and the extension portion may be folded back toward the inner sheet 23 side at the peripheral edge of the waist opening 5, such that the extended/folded-back portion covers the absorbent assembly 3's Y-direction end portion.

Further, in the front panel 2A/rear panel 2B of the diaper 1A of the foregoing first embodiment, the basis weight of the adhesive 8 in the section IP, of the lateral-side adhesion region IT, where the elastic member 24 is arranged is greater than the basis weight of the adhesive 8 in the section OP, of the side-seal adhesion region OT, where the elastic member 24 is arranged, and the basis weight of the adhesive 8 in the section IN, of the lateral-side adhesion region IT, which is located between adjacent elastic members 24, 24 is greater than the basis weight of the adhesive 8 in the section ON, of the side-seal adhesion region OT, which is located between adjacent elastic members 24, 24, as illustrated in FIG. 3. However, as in the diapers 1B and 1D of the second and fourth embodiments illustrated in FIGS. 8 and 10, the basis weights may be the same. Alternatively, as in the diaper 1E of the fifth embodiment illustrated in FIG. 11, the basis weight of the adhesive 8 in the section IP, of the lateral-side adhesion region IT, where the elastic member 24 is arranged may be smaller than the basis weight of the adhesive 8 in the section OP, of the side-seal adhesion region OT, where the elastic member 24 is arranged, and the basis weight of the adhesive 8 in the section IN, of the lateral-side adhesion region IT, which is located between adjacent elastic members 24, 24 may be smaller than the basis weight of the adhesive 8 in the section ON, of the side-seal adhesion region OT, which is located between adjacent elastic members 24, 24.

Further, the pull-on absorbent article may be, for example, a pull-on disposable diaper for an adult or an infant, or may be a pull-on sanitary napkin.

In relation to the foregoing embodiments, the following pull-on absorbent articles are also disclosed.

{1}

A pull-on absorbent article comprising:

an outer cover including an outer sheet that constitutes an outer surface, an inner sheet that is arranged on an inner surface side of the outer sheet, and a plurality of thread-form elastic members that are arranged in a stretched state between the outer sheet and the inner sheet; and an absorbent assembly that is fixed to the inner sheet of the outer cover; and both lateral side edge portions of the outer cover's front portion which is arranged on a front side of a wearer are bonded with respective lateral side edge portions of the outer cover's rear portion which is arranged on a rear side of the wearer so as to form a pair of side seals, a waist opening, and a pair of leg openings; wherein:

in a fixing part where the outer cover and the absorbent assembly are fixed, the outer cover has a weak-functioning region in which the plurality of elastic members are each divided into a plurality of pieces and the elastic members' elastic function is reduced;

in respective outer lateral sides of the weak-functioning region, lateral-side adhesion regions are formed in which the elastic members are fixed between the outer sheet and the inner sheet by an adhesive;

in the vicinity of the respective side seals, side-seal adhesion regions are formed in which the elastic members are fixed between the outer sheet and the inner sheet by an adhesive;

between the lateral-side adhesion region and the side-seal adhesion region, the elastic members are not fixed between the outer sheet and the inner sheet; and in each of the lateral-side adhesion regions and each of the side-seal adhesion regions, the basis weight of the adhesive in a section where the elastic member is arranged is higher than the basis weight of the adhesive in a section between adjacent elastic members, and sections having a high basis weight and sections having a low adhesive basis weight alternate repeatedly in a longitudinal direction of the pull-on absorbent article.

{2}

The pull-on absorbent article as set forth in clause {1}, wherein the elastic members which are each divided into a plurality of pieces in the weak-functioning region are fixed between the outer sheet and the inner sheet by the adhesive.

{3}

The pull-on absorbent article as set forth in clause {1} or {2}, wherein:

the basis weight of the adhesive in a section, of the lateral-side adhesion region, where the elastic member is arranged is greater than the basis weight of the adhesive in a section, of the side-seal adhesion region, where the elastic member is arranged; and the basis weight of the adhesive in a section, of the lateral-side adhesion region, which is located between adjacent elastic members is greater than the basis weight of the adhesive in a section, of the side-seal adhesion region, which is located between adjacent elastic members.

{4}

The pull-on absorbent article as set forth in clause {1} or {2}, wherein:

the basis weight of the adhesive in a section, of the lateral-side adhesion region, where the elastic member is arranged is smaller than the basis weight of the adhesive in a section, of the side-seal adhesion region, where the elastic member is arranged; and the basis weight of the adhesive in a section, of the lateral-side adhesion region, which is located between adjacent elastic members is smaller than the basis weight of the adhesive in a section, of the side-seal adhesion region, which is located between adjacent elastic members.

{5}

The pull-on absorbent article as set forth in clause {1} or {2}, wherein:

the basis weight of the adhesive in a section, of the lateral-side adhesion region, where the elastic member is arranged is the same as the basis weight of the adhesive in a section, of the side-seal adhesion region, where the elastic member is arranged; and the basis weight of the adhesive in a section, of the lateral-side adhesion region, which is located between adjacent elastic members is the same as the basis weight of the adhesive in a section, in the side-seal adhesion region, which is located between adjacent elastic members.

{6}

The pull-on absorbent article as set forth in clause {1} or {2}, wherein:

the basis weight of the adhesive in a section, of the lateral-side adhesion region, where the elastic member is arranged is the same as the basis weight of the adhesive in a section, of a side-seal inner adhesion region constituting the side-seal adhesion region, where the elastic member is arranged;

the basis weight of the adhesive in a section, of the lateral-side adhesion region, where the elastic member is arranged is greater than the basis weight of the adhesive in a section, of a side-seal outer adhesion region constituting the side-seal adhesion region, where the elastic member is arranged;

the basis weight of the adhesive in a section, of the lateral-side adhesion region, which is located between adjacent elastic members is the same as the basis weight of the adhesive in a section, of the side-seal inner adhesion region constituting the side-seal adhesion region, which is located between adjacent elastic members; and the basis weight of the adhesive in a section, of the lateral-side adhesion region, which is located between adjacent elastic members is greater than the basis weight of the adhesive in a section, of the side-seal outer adhesion region constituting the side-seal adhesion region, which is located between adjacent elastic members.

{7}

The pull-on absorbent article as set forth in any one of clauses {1} to {6}, wherein the absorbent assembly includes: a liquid-permeable topsheet; a liquid-impermeable or water-repellent backsheet; and a liquid-retentive absorbent member interposed between the topsheet and the backsheet.

{8}

The pull-on absorbent article as set forth in any one of clauses {1} to {7}, wherein the absorbent member includes: an absorbent core in which water-absorbing polymer particles are retained in an absorbent core constituted by a pulp fiber aggregate; and a core-wrap sheet that covers the absorbent core.

{9}

The pull-on absorbent article as set forth in any one of clauses {1} to {8}, wherein the outer sheet and the inner sheet are each a nonwoven fabric.

{10}

The pull-on absorbent article as set forth in any one of clauses {1} to {8}, wherein the outer sheet and the inner sheet are each a sheet made by integrating a nonwoven fabric and a film.

{11}

The pull-on absorbent article as set forth in any one of clauses {1} to {10}, wherein:

the outer cover includes a front panel arranged on the wearer's front side in the outer cover, and a rear panel arranged on the wearer's rear side in the outer cover;

a waist elasticized portion and a below-waist elasticized portion that are elastic in the longitudinal direction of the pull-on absorbent article are formed in each of the front panel and the rear panel; and in each of the front panel and the rear panel, the waist elasticized portion is formed more outward in the longitudinal direction (Y direction) of the pull-on absorbent article than the absorbent assembly's end portion in the longitudinal direction (Y direction).

{12}

The pull-on absorbent article as set forth in any one of clauses {1} to {11}, wherein:

the outer cover includes a front panel arranged on the wearer's front side in the outer cover, and a rear panel arranged on the wearer's rear side in the outer cover;

a waist elasticized portion and a below-waist elasticized portion that are elastic in the longitudinal direction of the pull-on absorbent article are formed in each of the front panel and the rear panel; and in each of the front panel and the rear panel, the below-waist elasticized portion is formed more inward in the longitudinal direction (Y direction) of the pull-on absorbent article than the waist elasticized portion.

{13}

The pull-on absorbent article as set forth in any one of clauses {1} to {12}, wherein:

the outer cover includes a front panel arranged on the wearer's front side in the outer cover, and a rear panel arranged on the wearer's rear side in the outer cover;

a waist elasticized portion and a below-waist elasticized portion that are elastic in the longitudinal direction of the pull-on absorbent article are formed in each of the front panel and the rear panel;

in the front panel, a plurality of the elastic members are arranged in the waist elasticized portion, and a plurality of the elastic members are arranged in the below-waist elasticized portion; and in the rear panel, a plurality of the elastic members are arranged in the waist elasticized portion, and a plurality of the elastic members are arranged in the below-waist elasticized portion.

{14}

The pull-on absorbent article as set forth in any one of clauses {1} to {13}, wherein:

the outer cover includes a front panel arranged on the wearer's front side in the outer cover, and a rear panel arranged on the wearer's rear side in the outer cover;

a waist elasticized portion and a below-waist elasticized portion that are elastic in the longitudinal direction of the pull-on absorbent article are formed in each of the front panel and the rear panel; and in the waist elasticized portion and the below-waist elasticized portion, the outer sheet and the inner sheet are bonded by a multitude of bonded portions formed in a scattered manner.

{15}

The pull-on absorbent article as set forth in any one of clauses {1} to {14}, wherein each of the plurality of elastic members is arranged so as to be passed between bonded portions that are adjacent to one another in the longitudinal direction (Y direction) of the pull-on absorbent article.

{16}

The pull-on absorbent article as set forth in any one of clauses {1} to {15}, wherein the adhesive includes: an elastic-member-applied adhesive that is applied to a peripheral surface of the elastic member, and that fixes the elastic member between the outer sheet and the inner sheet; and a sheet-applied adhesive that is applied in a planar manner to at least one of the outer sheet and the inner sheet, and that fixes the elastic member between the outer sheet and the inner sheet.

{17}

The pull-on absorbent article as set forth in any one of clauses {1} to {16}, wherein, in the lateral-side adhesion region, the sheet-applied adhesive is applied to the outer sheet in a strip-like form that is long in the longitudinal direction (Y direction) of the absorbent article, and the elastic-member-applied adhesive is applied to the peripheral surface of each elastic member forming the below-waist elasticized portion.

{18}

The pull-on absorbent article as set forth in any one of clauses {1} to {17}, wherein, in the side-seal adhesion region, the elastic-member-applied adhesive is applied to the peripheral surface of each elastic member forming the waist elasticized portion and each elastic member forming the below-waist elasticized portion.

{19}

The pull-on absorbent article as set forth in any one of clauses {1} to {18}, wherein each of the side seals is formed by a multitude of sealed portions that are arranged intermittently in the longitudinal direction (Y direction) of the absorbent article.

{20}

The pull-on absorbent article as set forth in any one of clauses {1} to {19}, wherein the sealed portions do not overlap the elastic members.

{21}

The pull-on absorbent article as set forth in any one of clauses {1} to {20}, wherein the pull-on absorbent article is a pull-on disposable diaper for an adult or an infant.

{22}

The pull-on absorbent article as set forth in any one of clauses {1} to {20}, wherein the pull-on absorbent article is a pull-on sanitary napkin.

INDUSTRIAL APPLICABILITY

According to the present invention, it is possible to provide a pull-on absorbent article in which elastic members are less likely to form creases in an absorbent member, thereby improving outer appearance, and also in which texture is improved and the elastic members are less likely to fall out.

The invention claimed is:

1. A pull-on absorbent article comprising:

an outer cover including an outer sheet that constitutes an outer surface, an inner sheet that is arranged on an inner surface side of the outer sheet, and a plurality of thread-form elastic members that are arranged in a stretched state between the outer sheet and the inner sheet; and an absorbent assembly that is fixed to the inner sheet of the outer cover; and both lateral side edge portions of the outer cover's front portion which is arranged on a front side of a wearer are bonded with respective lateral side edge portions of the outer cover's rear portion which is arranged on a rear side of the wearer so as to form a pair of side seals, a waist opening, and a pair of leg openings; wherein:

in a fixing part where the outer cover and the absorbent assembly are fixed, the outer cover has a weak-functioning region in which the plurality of elastic members are each divided into a plurality of pieces and the elastic members' elastic function is reduced;

in respective outer lateral sides of the weak-functioning region, lateral-side adhesion regions are formed in which the elastic members are fixed between the outer sheet and the inner sheet by an adhesive;

in the vicinity of the respective side seals, side-seal adhesion regions are formed in which the elastic members are fixed between the outer sheet and the inner sheet by an adhesive;

between the lateral-side adhesion region and the side-seal adhesion region, the elastic members are not fixed between the outer sheet and the inner sheet; and in each of the lateral-side adhesion regions and each of the side-seal adhesion regions, the basis weight of the adhesive in a section where the elastic member is arranged is higher than the basis weight of the adhesive in a section between adjacent elastic members, and sections having a high basis weight and sections having a low adhesive basis weight alternate repeatedly in a longitudinal direction of the pull-on absorbent article.

2. The pull-on absorbent article according to claim 1, wherein the elastic members which are each divided into a plurality of pieces in the weak-functioning region are fixed between the outer sheet and the inner sheet by the adhesive.

3. The pull-on absorbent article according to claim 1, wherein:

the basis weight of the adhesive in a section, of the lateral-side adhesion region, where the elastic member is arranged is greater than the basis weight of the adhesive in a section, of the side-seal adhesion region, where the elastic member is arranged; and the basis weight of the adhesive in a section, of the lateral-side adhesion region, which is located between adjacent elastic members is greater than the basis weight of the adhesive in a section, of the side-seal adhesion region, which is located between adjacent elastic members.

4. The pull-on absorbent article according to claim 1, wherein:

the basis weight of the adhesive in a section, of the lateral-side adhesion region, where the elastic member is arranged is smaller than the basis weight of the adhesive in a section, of the side-seal adhesion region, where the elastic member is arranged; and the basis weight of the adhesive in a section, of the lateral-side adhesion region, which is located between adjacent elastic members is smaller than the basis weight of the adhesive in a section, of the side-seal adhesion region, which is located between adjacent elastic members.

5. The pull-on absorbent article according to claim 1, wherein:
the basis weight of the adhesive in a section, of the lateral-side adhesion region, where the elastic member is arranged is the same as the basis weight of the adhesive in a section, of the side-seal adhesion region, where the elastic member is arranged; and
the basis weight of the adhesive in a section, of the lateral-side adhesion region, which is located between adjacent elastic members is the same as the basis weight of the adhesive in a section, in the side-seal adhesion region, which is located between adjacent elastic members.

6. The pull-on absorbent article according to claim 1, wherein:
the basis weight of the adhesive in a section, of the lateral-side adhesion region, where the elastic member is arranged is the same as the basis weight of the adhesive in a section, of a side-seal inner adhesion region constituting the side-seal adhesion region, where the elastic member is arranged;
the basis weight of the adhesive in a section, of the lateral-side adhesion region, where the elastic member is arranged is greater than the basis weight of the adhesive in a section, of a side-seal outer adhesion region constituting the side-seal adhesion region, where the elastic member is arranged;
the basis weight of the adhesive in a section, of the lateral-side adhesion region, which is located between adjacent elastic members is the same as the basis weight of the adhesive in a section, of the side-seal inner adhesion region constituting the side-seal adhesion region, which is located between adjacent elastic members; and
the basis weight of the adhesive in a section, of the lateral-side adhesion region, which is located between adjacent elastic members is greater than the basis weight of the adhesive in a section, of the side-seal outer adhesion region constituting the side-seal adhesion region, which is located between adjacent elastic members.

7. The pull-on absorbent article according to claim 1, wherein:
the outer cover includes a front panel arranged on the wearer's front side in the outer cover, and a rear panel arranged on the wearer's rear side in the outer cover;
a waist elasticized portion and a below-waist elasticized portion that are elastic in the lateral direction of the pull-on absorbent article are formed in each of the front panel and the rear panel; and
in each of the front panel and the rear panel, the waist elasticized portion is formed more outward in the longitudinal direction of the pull-on absorbent article than the absorbent assembly's end portion in the longitudinal direction.

8. The pull-on absorbent article according to claim 1, wherein:
the outer cover includes a front panel arranged on the wearer's front side in the outer cover, and a rear panel arranged on the wearer's rear side in the outer cover;
a waist elasticized portion and a below-waist elasticized portion that are elastic in the lateral direction of the pull-on absorbent article are formed in each of the front panel and the rear panel; and
in each of the front panel and the rear panel, the below-waist elasticized portion is formed more inward in the longitudinal direction of the pull-on absorbent article than the waist elasticized portion.

9. The pull-on absorbent article according to claim 1, wherein:
the outer cover includes a front panel arranged on the wearer's front side in the outer cover, and a rear panel arranged on the wearer's rear side in the outer cover;
a waist elasticized portion and a below-waist elasticized portion that are elastic in the lateral direction of the pull-on absorbent article are formed in each of the front panel and the rear panel;
in the front panel, a plurality of the elastic members are arranged in the waist elasticized portion, and a plurality of the elastic members are arranged in the below-waist elasticized portion; and
in the rear panel, a plurality of the elastic members are arranged in the waist elasticized portion, and a plurality of the elastic members are arranged in the below-waist elasticized portion.

10. The pull-on absorbent article according to claim 1, wherein:
the outer cover includes a front panel arranged on the wearer's front side in the outer cover, and a rear panel arranged on the wearer's rear side in the outer cover;
a waist elasticized portion and a below-waist elasticized portion that are elastic in the lateral direction of the pull-on absorbent article are formed in each of the front panel and the rear panel; and
in the waist elasticized portion and the below-waist elasticized portion, the outer sheet and the inner sheet are bonded by a multitude of bonded portions formed in a scattered manner.

11. The pull-on absorbent article according to claim 1, wherein each of the plurality of elastic members is arranged so as to be passed between bonded portions that are adjacent to one another in the longitudinal direction of the pull-on absorbent article.

12. The pull-on absorbent article according to claim 1, wherein the adhesive includes: an elastic-member-applied adhesive that is applied to a peripheral surface of the elastic member, and that fixes the elastic member between the outer sheet and the inner sheet; and a sheet-applied adhesive that is applied in a planar manner to at least one of the outer sheet and the inner sheet, and that fixes the elastic member between the outer sheet and the inner sheet.

13. The pull-on absorbent article according to claim 12, wherein, in the lateral-side adhesion region, the sheet-applied adhesive is applied to either the outer sheet or the inner sheet in a strip-like form that is long in the longitudinal direction of the absorbent article, and the elastic-member-applied adhesive is applied to the peripheral surface of each elastic member forming the below-waist elasticized portion.

14. The pull-on absorbent article according to claim 12, wherein, in the lateral-side adhesion region, the sheet-applied adhesive is applied to the outer sheet in a strip-like form that is long in the longitudinal direction of the absorbent article, and the elastic-member-applied adhesive is applied to the peripheral surface of each elastic member forming the below-waist elasticized portion.

15. The pull-on absorbent article according to claim 12, wherein, in the side-seal adhesion region, the elastic-member-applied adhesive is applied to the peripheral surface of each elastic member forming the waist elasticized portion and each elastic member forming the below-waist elasticized portion.

16. The pull-on absorbent article according to claim 15, wherein the sheet-applied adhesive is not applied in the side-seal adhesion region.

17. The pull-on absorbent article according to claim 1, wherein each of the side seals is formed by a multitude of sealed portions that are arranged intermittently in the longitudinal direction of the absorbent article.

18. The pull-on absorbent article according to claim 17, wherein the sealed portions do not overlap the elastic members.

19. The pull-on absorbent article according to claim 1, wherein the pull-on absorbent article is a pull-on disposable diaper for an adult or an infant.

20. The pull-on absorbent article according to claim 1, wherein the pull-on absorbent article is a pull-on sanitary napkin.

* * * * *